(12) United States Patent
Preiss-Bloom et al.

(10) Patent No.: US 11,317,957 B2
(45) Date of Patent: May 3, 2022

(54) FIBER REINFORCED BIOCOMPOSITE THREADED IMPLANTS

(71) Applicant: OSSIO, Ltd., Caesarea (IL)

(72) Inventors: Orahn Preiss-Bloom, Caesarea (IL);
Taly Pnina Lindner, Caesarea (IL);
Ilan Oleg Uchitel, Caesarea (IL); Ilya Krivoruk, Caesarea (IL)

(73) Assignee: OSSIO, LTD., Caesarea (IL)

( * ) Notice: Subject to any disclaimer, the term of this patent is extended or adjusted under 35 U.S.C. 154(b) by 239 days.

(21) Appl. No.: 16/637,363

(22) PCT Filed: Sep. 6, 2018

(86) PCT No.: PCT/IB2018/056809
§ 371 (c)(1),
(2) Date: Feb. 7, 2020

(87) PCT Pub. No.: WO2019/049062
PCT Pub. Date: Mar. 14, 2019

(65) Prior Publication Data
US 2021/0369314 A1    Dec. 2, 2021

Related U.S. Application Data

(60) Provisional application No. 62/555,070, filed on Sep. 7, 2017.

(51) Int. Cl.
*A61B 17/86* (2006.01)
*A61L 31/12* (2006.01)
(Continued)

(52) U.S. Cl.
CPC .......... *A61B 17/866* (2013.01); *A61B 17/863* (2013.01); *A61L 31/128* (2013.01);
(Continued)

(58) Field of Classification Search
CPC ............................ A61B 17/866; A61B 17/863
See application file for complete search history.

(56) References Cited

U.S. PATENT DOCUMENTS 4,750,905 A   6/1988 Koeneman
5,181,930 A   1/1993 Dumbleton
(Continued)

FOREIGN PATENT DOCUMENTS

CN   101420991 A   4/2009
CN   101942709 A   1/2011
(Continued)

OTHER PUBLICATIONS

Canadian Office Action for App. No. CA2,955,392, dated Sep. 27, 2021, 15 pages.
(Continued)

*Primary Examiner* — Christian A Sevilla
(74) *Attorney, Agent, or Firm* — Graeser Associates International Inc.; D'vorah Graeser

(57) ABSTRACT

A threaded medical implant comprising a biocomposite, said biocomposite comprising a polymer and a plurality of reinforcement fibers, wherein a weight percentage of a mineral composition within the biocomposite medical implant is in the range of 30-60%, wherein an average diameter of said fibers is in a range of 1-100 microns, said medical implant being threaded with a plurality of threads; wherein said fibers comprise a plurality of helical fibers and a plurality of longitudinal fibers; wherein a weight to weight percent ratio of said helical to said longitudinal fibers is from 90:10 to 10:90.

31 Claims, 13 Drawing Sheets

(51) Int. Cl.
*A61L 31/14* (2006.01)
*B29C 70/08* (2006.01)
*B29C 70/86* (2006.01)
*B29K 267/00* (2006.01)

(52) U.S. Cl.
CPC .......... *A61L 31/148* (2013.01); *B29C 70/081* (2013.01); *B29C 70/86* (2013.01); *A61B 17/864* (2013.01); *B29K 2267/043* (2013.01)

(56) References Cited

U.S. PATENT DOCUMENTS

| | | | |
|---|---|---|---|
| 5,192,330 A | 3/1993 | Chang | |
| 5,679,299 A | 10/1997 | Gilbert | |
| 6,171,338 B1 | 1/2001 | Talja | |
| 6,306,140 B1 | 10/2001 | Siddiqui | |
| 6,511,511 B1 * | 1/2003 | Slivka | A61F 2/30756 623/16.11 |
| 6,602,293 B1 | 8/2003 | Biermann | |
| 8,709,055 B2 * | 4/2014 | Beyar | A61B 17/1631 606/301 |
| 9,456,890 B2 | 10/2016 | Day | |
| 2008/0255561 A1 | 10/2008 | Tormala | |
| 2009/0258965 A1 | 10/2009 | Lassila | |
| 2010/0121463 A1 | 5/2010 | Toermaelae | |
| 2013/0204368 A1 | 8/2013 | Prevost | |
| 2013/0296500 A1 | 11/2013 | Clay | |
| 2016/0011369 A1 | 1/2016 | Doyle | |
| 2016/0113695 A1 * | 4/2016 | Globerman | B29C 70/00 606/309 |
| 2017/0181785 A1 | 6/2017 | Beyar | |
| 2017/0246356 A1 * | 8/2017 | Preiss-Bloom | A61L 31/148 |
| 2021/0299332 A1 | 9/2021 | Dias | |
| 2022/0008615 A1 | 1/2022 | Cige | |

FOREIGN PATENT DOCUMENTS

| | | |
|---|---|---|
| CN | 102281907 A | 12/2011 |
| CN | 102421716 A | 4/2012 |
| CN | 103747813 A | 4/2014 |
| CN | 104188706 A | 12/2014 |
| EP | 0373294 A2 | 6/1990 |
| EP | 2243500 A1 | 10/2010 |
| EP | 2243749 A1 | 10/2010 |
| EP | 3320877 | 5/2018 |
| EP | 3320877 A1 | 5/2018 |
| JP | H02121652 | 5/1990 |
| JP | 2010526200 | 7/2010 |
| JP | 2012524569 | 10/2012 |
| WO | 9609014 | 3/1996 |
| WO | 9609014 A1 | 3/1996 |
| WO | 2008095046 A2 | 8/2008 |

OTHER PUBLICATIONS

Chinese Office Action (with English translation) for App. No. CN201780053086.6, dated Oct. 19, 2021, 15 pages.
Chinese Office Action for App. No. CN201880057783.3, dated Dec. 2, 2021, 15 pages.
Indian Examination Report for App. No. IN201827049363, dated Nov. 18, 2021, 5 pages.
Office Action dated Sep. 23, 2021 for U.S. Appl. No. 16/311,784 (pp. 1-11).
Chinese Office Action for App. No. CN201780053086.6, dated Feb. 18, 2021, 23 pages.
English translation of Japanese Office Action for App. No. JP2018-567587, dated Mar. 23, 2021, 4 pages.
Office Action dated Apr. 7, 2021 for U.S. Appl. No. 16/311,784 (pp. 1-11).
Wei Junjie, "Medical Organic Chemistry Learning Guide", p. 300, Heilongjiang Science and Technology Press, Jan. 19.
Li Sijiao, "Modern Chromatographic Analysis", p. 118, National Defense Industry Press, Jun. 2014.
Extended European Search Report for App. No. EP18853365.7, dated May 4, 2021, 7 pages.
Australian Examination Report No. 1 for App. No. AU2017287968, dated Aug. 31, 2021, 3 pages.
Chinese Office Action (including English translation) for App. No. CN201780025291.1, dated Aug. 10, 2021, 12 pages.
European Patent Office Communication pursuant to Article 94(3) EPC for App. No. EP17819487.4, dated Jun. 21, 2021, 5 pages.
Extended European Search Report for App. No. EP18890927.9, dated Jul. 27, 2021, 7 pages.
Chinese Third Office Action (with English translation) for App. No. CN201780053086.6, dated Feb. 16, 2022, 13 pages.
European Patent Office Communication pursuant to Article 94(3) EPC for App. No. EP17763876.4, dated Jan. 4, 2022, 8 pages.
Japanese Office Action (including English translation) for App. No. JP2018-567587, dated Jan. 5, 2022, 5 pages.
Korean Office Action (including English translation) for App. No. KR10-2019-7001863, dated Jan. 20, 2022, 13 pages.
Office Action (Notice of Allowance and Fees Due (PTOL-85)) dated Feb. 8, 2022 for U.S. Appl. No. 16/311,784 (pp. 1-6).
Office Action (Notice of Allowance and Fees Due (PTOL-85)) dated Feb. 22, 2022 for U.S. Appl. No. 16/311,784 (pp. 1-3).

* cited by examiner

FIBER REINFORCED BIOCOMPOSITE THREADED IMPLANTS

BACKGROUND

Permanent Orthopedic Implant Materials

Medical implants can be manufactured from metals, alloys, ceramics or both degradable and stable composites. In load-bearing, orthopedic applications that require high strength, usually stainless steel or titanium alloys are used. Metal implants have a long history of successful use in orthopedic surgery but also carry many risks for complications. Although these materials are inert, they are also used in situations in which the need for the implant is only temporary, like in fracture fixation. In the case of metal rods and plates for fracture fixation, a second surgery for device removal may be recommended about one year after confirmation of osseous union. Implant removal causes additional risk and added morbidity for the patient, occupies the availability of clinics, and increases the overall procedure costs. If the device is not removed, it may cause remodeling of the bone. Such remodeling may in turn weaken the bone due to stress shielding or inflammation of the host tissue. The stress shielding can occur due to the high stiffness (modulus) and strength of the metals compared to the stiffness and strength of the cortical bone, so that the metal stresses the bone, which can result in periprosthetic fractures or loss of bone strength.

Examples of load-bearing medical implants that have traditionally been constructed of metal alloys include bone plates, rods, screws, tacks, nails, clamps, and pins for the fixation of bone fractures and/or osteotomies to immobilize the bone fragments for healing. Other examples include cervical wedges, lumbar cages and plates and screws for vertebral fusion and other operations in spinal surgery.

Biostable polymers and their composites e.g. based on polymethacrylate (PMMA), ultra high molecular weight polyethylene (UBMWPE), polytetrafluoroethylene (PTFE), polyetheretherketone (PEEK), polysiloxane and acrylic polymers have also been used to manufacture medical implants. These materials are not biodegradable or bioresorbable and therefore face many of the same limitations as the metals when used for medical implant applications, for example they may require a second surgery for replacing or removing the implant at some point of the lifetime of the implant. Furthermore, these materials are weaker (less strong and stiff) than metal such that they are more susceptible to mechanical failure, particularly after repeated dynamic loading (i.e. through material fatigue or creep).

Existing Degradable Polymer Medical Implants

Resorbable polymers have been used to develop resorbable implants, which can also be referred to as absorbable, bioabsorbable, or biodegradable implants. The advantage of using biocompatible, resorbable polymers is that the polymers, and thus the implant, resorb in the body and release non-toxic degradation products that are metabolized by the metabolic system. Polymers, including polylactic and polyglycolic acids and polydioxanone, are resorbable biocompatible materials that are currently used as orthopedic plates, rods, anchors, pins or screws for non-load bearing medical implant applications, such as craniofacial applications. These medical implant materials offer the advantage of eventual resorption, eliminating the need for later removal, while allowing stress transfer to the remodeling fracture. However, current bioabsorbable materials and implants do not have mechanical properties to match metallic implants. The mechanical strength and modulus (approximately 3-5 GPa) of non-reinforced resorbable polymers, is insufficient to support fractured cortical bone, which has an elastic modulus in the range of approximately 15-20 GPa (Snyder S M, et al. measured the bending modulus of human tibial bone to be about 17.5 GPa Snyder S M Schneider E, *Journal of Orthopedic Research, Vol. 9*, 1991, pp. 422-431). Therefore, the indications of existing medical implants constructed from resorbable polymers are limited and their fixation usually requires protection from motion or significant loading. These devices are only a consideration when fixation of low stress areas is needed (i.e. non-load bearing applications) such as in pediatric patients or in medial malleolar fractures, syndesmotic fixation, maxillofacial, or osteochondral fractures in adults.

Reinforced Degradable Polymer Materials

Recently, reinforced polymer materials with improved strength and stiffness (modulus) have been introduced. These biodegradable composites comprise polymers reinforced by fillers, usually in fiber form. In composite materials, usually a relatively flexible matrix (i.e. a polymer) is combined with a stiff and strong reinforcement material to enhance the mechanical properties of the composite matrix. For example, biodegradable glass or mineral material can be used to improve the stiffness and strength of a biodegradable polymer matrix. In the prior art, several attempts to produce such a composite were reported where bioactive glass particles, hydroxyapatite powder, or short glass fibers were used to enhance the properties of a biodegradable polymer. In most cases, the strength and stiffness of these composites is lower than cortical bone or becomes lower than cortical bone following rapid degradation in a physiological environment. Therefore, the majority of these composite materials are not appropriate for use in load-bearing medical implant applications. However, biodegradable composites with strength and stiffness equivalent to or greater than cortical bone have recently been reported, for example a biodegradable composite comprising a biodegradable polymer and 20-70 vol % glass fibers (WO2010128039 A1). Other composite material implants, for example formed of polymer reinforced with fibers, are disclosed in U.S. Pat. Nos. 4,750,905, 5,181,930, 5,397,358, 5,009,664, 5,064,439, 4,978,360, 7,419,714, the disclosures of which are incorporated herein by reference Degradation Mechanism of Reinforced Degradable Polymer Materials When biodegradable composites are used for load-bearing medical implant applications, such as to fixate bone fractures, the mechanical properties of the medical implant must be retained for an extended period. Degradation of the composite will result in premature loss of implant strength or stiffness and can lead to implant function failure, such as insufficient fixation of bone segments resulting in improper bone healing.

Biodegradable composites will begin to hydrolytically degrade once they come into contact with body fluid. This degradation can be a result of degradation of the biodegradable polymer, reinforcing filler, or both. Such degradation in an aqueous environment, such as the physiological environment, can particularly result in a sharp drop-off of mechanical strength and stiffness in certain reinforced polymer materials that are reinforced by inorganic compounds. Where the absorbable polymer matrix is organic material, and the fillers are inorganic compounds, the adhesion between the absorbable polymer matrix and the filler may be reduced by degradation of either the polymer or filler in the aqueous environment and become rapidly reduced such that the initial mechanical properties of the reinforced polymer drop-off rapidly and become less than desirable for adequate load-bearing performance. Aside from the degradation of the polymer and filler separately, poor polymer to reinforcement interface interaction and adhesion can result in early failure at the interface in a aqueous environment, thereby resulting in sharp mechanical property drop off as the reinforcement detaches from the polymer and the reinforcing effect of the filler is lost.

Törmälä et al. (WO 2006/114483) described a composite material containing two reinforcing fibers, one polymeric and one ceramic, in a polymer matrix and reported good initial mechanical results (bending strength of 420+/−39 MPa and bending modulus of 21.5 GPa) equivalent to the properties of cortical bone. However, the prior art teaches that bioabsorbable composites reinforced with absorbable glass fibers, have a high initial bending modulus but that they rapidly lose their strength and modulus in vitro.

While improved interfacial bonding (such as covalent bonding) between the polymer and reinforcement can significantly prolong reinforced bioabsorbable polymer mechanical property retention in an aqueous environment (WO2010128039 A1), continued hydrolysis of the polymer, reinforcement, or interface between the two will result in loss of mechanical properties over time. Since osseous union may take several months or longer, even the prolonged mechanical property degradation profile in covalently bonded reinforced bioabsorbable polymers may be insufficient for optimal function of medical implants used for load-bearing orthopedic applications.

An example of strength loss in a reinforced degradable polymer implant is described with regard to self-reinforced poly-L-lactic acid (Majola A et al., *Journal of Materials Science Materials in Medicine, Vol.* 3, 1992, pp. 43-47). There, the strength and strength retention of self-reinforced poly-L-lactic acid (SR-PLLA) composite rods were evaluated after intramedullary and subcutaneous implantation in rabbits. The initial bending strength of the SR-PLLA rods was 250-271 MPa. After intramedullary and subcutaneous implantation of 12 weeks the bending strength of the SR-PLLA implants was 100 MPa.

Co- and terpolyesters of PLA, PGA and PCL are of interest in the tailoring of the optimal polymer for resorbable composite material for medical devices. The choice of monomer ratio and molecular weight significantly affects the strength elasticity, modulus, thermal properties, degradation rate and melt viscosity of resorbable composite materials and all of these polymers are known to be degradable in aqueous conditions, both in vitro and in vivo. Two stages have been identified in the degradation process: First, degradation proceeds by random hydrolytic chain scission of the ester linkages which decreases the molecular weight of the polymers. In the second stage measurable weight loss in addition to chain scission is observed. The mechanical properties are mainly lost or at least a remarkable drop will be seen in them at the point where weight loss starts. Degradation rate of these polymers is different depending on the polymer structure: crystallinity, molecular weight, glass transition temperature, block length, racemization and chain architecture. (*Middleton J C, Tipton A J, Biomaterials* 21, 2000, 2335-2346)

The Unsolved Problem of Mineral Content in Orthopedic Implants

As previously described, attempts have been made to produce orthopedic fixation implants from bioabsorbable polymers such as poly lactic acid (PLA). However, these implants derived their mechanical properties solely from the PLA acidic polymer chains. Thus, their strength was limited (a fraction of the strength and modulus of bone) and the acidic burst degradation process of these bioabsorbable polymer implants resulted in problematic local tissue response (cysts, abcesses, etc). The bone attachment to these implants was poor.

Manufacturers have responded to the inflammatory local tissue response and poor bone attachment of bioabsorbable fixation devices by mixing various mineral compositions into the bioabsorbable polymer compositions. For mineral compositions, companies have used minerals or mineral compositions with osteoconductive properties. Some use Tricalcium phosphate, some use hydroxyapatite, some use calcium sulfate, some use mixtures of these. These mixed composition implants are called "biocomposite" implants and incorporate 25-35% mineral and the mineral powder is evenly distributed into the polymer composition.

Unfortunately, the mineral additive in these biocomposite implants reduces the mechanical properties of the implants since the mechanical strength of these implants derives from the bioabsorbable polymer and there is less polymer in the implant once the mineral composition has been added. Thus, biocomposite implants tend to be more brittle than equivalent implants comprised entirely of bioabsorbable polymers. Higher amounts of mineral than the existing 25-35% cannot be used since the implant will be lacking in mechanical properties.

On the other hand, without the mineral composition, the long term implantation results of existing biocomposite implants are problematic. These implants still suffer from the inflammatory tissue response that has plagued bioabsorbable polymer implants. For example, in ACL interference screws comprised of biocomposite compositions, it has been demonstrated (Cox C L et al. J Bone Joint Surg Am. 2014; 96:244-50) that biocomposite screws result in a very high percentage of inflammatory reactions (cysts, edema). Furthermore, they don't really encourage biointegration. As the article concludes "Even though these newer-generation bioabsorbable screws were designed to promote osseous integration, no tunnel narrowing was noted".

Besides for these inflammatory problems, the current biocomposite screws also are lacking in sufficient mechanical properties (Mascarenhas et al. Arthroscopy: J Arthroscopic & Related Surg 2015: 31(3): pp 561-568). As the article concludes, "The major findings of this study were prolonged knee effusion, increased femoral tunnel widening, and increased screw breakage associated with Bioabsorbable Interference Screw use".

On a mechanical level, higher percentage level of mineral composition in a biocomposite implant can lead to poor mechanical results and specifically mechanical results that are inferior to the mechanical results of implants comprised solely of bioabsorbable polymer. For example, the effect of different percentages of beta-tricalcium phosphate ($\beta$TCP) on the mechanical properties of a PLA based biocomposite have been studied (Ferri J M et al. J Composite Materials. 2016; 0(0): 1-10).

In that study, it was shown that higher percentages of $\beta$TCP result in a significant loss of tensile strength for the PLA-$\beta$TCP biocomposite, shown in FIG. 1 of that reference.

Furthermore, an increase in the percentage of $\beta$TCP results in a significant loss in the amount of energy the biocomposite can absorb, as measured as Charpy's impact energy. This is a very important parameter in orthopedic implants since a key property of an orthopedic implant is the ability to withstand impact without fracturing. Table 2 (taken from the above reference) demonstrates this problem.

TABLE 2

Shore D hardness values and Charpy's absorbed energy of PLA/β-TCP composites in terms of the β-TCP weight percent.

| Wt % β-TCP | Shore D hardness | Charpy's impact energy (J/m$^2$) |
|---|---|---|
| 0 | 71 ± 1 | 1.85 ± 0.2 |
| 10 | 74 ± 1 | 1.68 ± 0.3 |
| 20 | 75 ± 1 | 1.40 ± 0.2 |
| 30 | 77 ± 1 | 1.25 ± 0.1 |
| 40 | 79 ± 1 | 1.10 ± 0.2 |

Reinforced Biocomposite Threaded Implants

Medical screws or medical implants that include screw threads have been described for use in a number of surgical applications and, specifically, for a number of applications in orthopedic fixation. These applications primarily include bone or bone fragment to bone fixation and attachment of soft tissue (ligaments, tendons, etc) to bone. The types of threaded medical implants that have been previously described included headed screws, headless compression screws, progressively threaded headless compression screws, suture anchors, interference screws, etc. (i.e. US 20080234730 A1, U.S. Pat. Nos. 5,275,601 A, 6,743,233 B1, 5,891,46, 7,731,738 B2).

In many cases, the threaded medical implant or screw is inserted mostly or entirely into bone tissue. It would therefore be helpful for the implant or screw to be comprised of a biocomposite composite that would facilitate attachment and ingrowth of the surrounding bone tissue onto and into the implant. Such biocomposite screw would preferably be comprised of a significant amount of osteoconductive mineral, with the remainder of the screw comprised of a bioabsorbable polymer. Biocomposite screws have been previously described (U.S. Pat. No. 5,275,601. Felfel R M, et al, Bioresorbable composite screws manufactured via forging process: Pull-out, shear, flexural and degradation characteristics, Journal of mechanical behavior of biomedical materials 18 (2913) 109-122).

Unfortunately, the mechanical properties of previously described biocomposite screws have been limited to the mechanical strength of bioabsorbable polymers, which is only a fraction of the mechanical strength of cortical bone.

SUMMARY OF THE INVENTION

There is a great need for a biocomposite threaded implant comprising reinforced bioabsorbable polymer material exhibiting improved mechanical properties for use in load-bearing medical implant applications, such as structural fixation for load-bearing purposes, where the high strength and stiffness of the implant are retained at a level equivalent to or exceeding cortical bone for a period at least as long as the maximum bone healing time.

The present invention, in at least some embodiments, relates to a biocomposite threaded implant that is reinforced by mineral fibers. The internal structures and architectures of the implant, in particular the organization and orientation of the fibers within the polymer matrix, provide the implant with beneficial mechanical properties that allow the implant to function effectively in orthopedic fixation. Furthermore, these structures allow the implant to have these mechanical properties while still enabling the ingrowth of bone from surrounding tissues.

The present invention, in at least some embodiments, specifically refers to screws and threaded implants comprised of a biocomposite composition comprising bioabsorbable polymer and reinforcing mineral fibers.

The present invention, in at least some embodiments, overcomes the limitations of previous biocomposite medical screws and threaded implants by providing such implants comprising a biocomposite material composition with a high percentage of mineral content and yet with superior mechanical properties. Preferably the mineral composition is provided by a reinforcing fiber made from the mineral composition.

Preferably, the weight percentage of the mineral composition within the biocomposite medical implant is in the range of 30-60%, or 40-90%, more preferably the weight percentage is in the range of 40%-70%, more preferably in the range of 40%-65%, and even more preferably the weight percentage is in the range of 45%-60%.

Surprisingly, the inventors have found that such a high percentage or amount of mineral content can yield implants with superior mechanical properties.

Additionally, previous attempts to construct implants with higher mineral contents failed because biocomposite implants are typically injection molded. The flow properties of a composite with an amount or percentage of mineral content in the above high range are more challenging to injection mold.

These preferential ranges derive from a critical balance between biocompatibility (quiescent inflammatory response) and strong mechanical properties. As discussed previously, higher mineral content percentage in the medical implant has potential beneficial in increasing biocompatibility and safety profile of the implant with the surrounding tissues, especially bony tissues. However, mineral content that is too high can result in an undesirable reduction in mechanical properties. In some cases a reduction in implant mechanical properties will be seen immediately. In other cases, high mineral content can result in an accelerated mechanical degradation process wherein the implant will lose its mechanical properties at an accelerated rate and thereby lose its ability to provide mechanical fixation for an in vivo time period sufficient to support tissue (and especially orthopedic tissue) healing.

The present invention, in at least some embodiments, which may be combined with any other embodiment or sub-embodiment as described herein, comprises a medical implant comprising a biocomposite, the biocomposite comprising a polymer and a plurality of reinforcement fibers, wherein a weight percentage of a mineral composition within the biocomposite medical implant is in the range of 30-60%, wherein an average diameter of the fibers is in a range of 1-100 microns, the medical implant being threaded with a plurality of threads; wherein the fibers comprise a plurality of helical fibers and a plurality of longitudinal fibers; wherein a weight to weight percent ratio of the helical to the longitudinal fibers is from 90:10 to 10:90.

Optionally the weight to weight percent ratio is from 80:20 to 20:80. Optionally the weight to weight percent ratio is from 33:66 to 66:33. Optionally a winding angle of the helical layers is in a range of from 5 to 60 degrees. Optionally the winding angle of the helical fibers ranges from 20 degrees to 45 degrees.

Optionally the implant threads are of a constant pitch or of a variable pitch. Optionally the helical fibers are of a constant pitch and the pitch angle is in the range of 1 to 45 degrees, optionally in the range of 5 to 20 degrees or alternatively in the range of 20 to 45 degrees. Alternatively and optionally, the threads are of a variable pitch angle and the pitch angle is in the range of 0 to 90 degrees, preferably in the range of 0 to 45 degrees, and more preferably in the range of 20 to 45.

Optionally the biocomposite is arranged in a plurality of layers, wherein fibers in each layer are discontinuous to an adjacent layer. Optionally helical fibers in a first layer are wound clockwise while helical fibers in an adjacent layer are wound counterclockwise. Optionally the winding angle is wound toward an area of greater torsional stress of the implant. Optionally an angle between the thread and the angle of the helical fibers is in a range of from 0 to 60 degrees, preferably in the range of 40 to 60 degrees, or optionally in the range of 0 to 20 degrees.

Optionally the implant has a longitudinal axis and wherein longitudinal fibers in a first layer have a first angle with respect to the longitudinal axis and longitudinal fibers in a second layer have a second angle with respect to the longitudinal axis. Optionally the angle range between implant's axis and longitudinal fibers is in the range of −5° to 5°.

The implant may optionally further comprise a plurality of helical layers and a plurality of longitudinal layers, wherein the helical and longitudinal layers are each grouped into discrete region of wall thickness of the implant such that they form concentric regions in the implant.

Optionally at least one concentric longitudinal fiber region is internal to at least one concentric helical fiber region. Optionally at least one concentric helical fiber region is external to at least one concentric longitudinal fiber region.

Optionally a thickness of the concentric regions is in a range of from 0.2 mm up to 50% of the wall thickness of an implant. Optionally the thickness of the concentric regions is in a range of from 0.2 mm to 4 mm. Optionally the thickness is in a range from 0.2 mm to 2 mm, and preferably in a range from 0.2 mm to 1 mm.

Optionally a number of helical layers is in a range of from 1 to 15, preferably in the range of 1 to 10, more preferably in the range of 4 to 6, or optionally in the range of 8 to 15. Optionally the diameter of the threaded implant is in the range of 2 to 4 mm and the number of helical layers is in the range of 2-12, preferably 3-8. Optionally the diameter of the threaded implant is in the range of 3.5 mm to 8 mm and the number of helical layers is in the range of 4-18, preferably 6-14. Optionally the number of longitudinal layers is in a range of from 1 to 15, preferably in the range of 1 to 10, more preferably in the range of 4-6, or optionally in the range of 1-5. Optionally the diameter of the threaded implant is in the range of 2 to 4 mm and the number of longitudinal layers is in the range of 1-5, preferably 1-4.

Optionally the diameter of the threaded implant is in the range of 3.5 mm to 8 mm and the number of longitudinal layers is in the range of 1-10, preferably 2-7. Optionally a number of fibers in the thickness of each helical layer is in a range of from 2-20, preferably in the range from 8-15. Optionally a number of fibers in the thickness of each longitudinal layer is in a range of from 2-20, preferably in the range from 8-15. Optionally a number of longitudinal layers is in a range of from 1 to 10, preferably from 4 to 10, and more preferably from 6 to 8. Optionally an angle between the longitudinal layers is in a range of −5° to 5°.

The implant may optionally further comprise at least one layer of a plurality of layers comprising a plurality of continuous fibers along the layer, and at least one other layer comprising a plurality of chopped fibers, wherein a length of the chopped fibers is less than a length of the at least one other layer.

Optionally an average length of chopped fiber is <10% of the length of the implant and preferably <5% of the implant.

Optionally the implant comprises a plurality of different portions, and wherein a concentration of the chopped fibers varies over the plurality of portions of the implant. Optionally the concentration of the chopped fibers varies from 1% to 50% of the biocomposite, preferably 2% to 10% or alternatively 1% to 10% weight per weight percent.

Optionally the implant comprises a head and a body, and wherein the chopped fibers are located at the head for reinforcement. Optionally the implant comprises a plurality of threads, and wherein the chopped fibers are located at the threads for reinforcement.

Optionally any implant as described herein is cannulated.

Optionally the implant comprises a wall, wherein the wall comprises an inner segment and an outer segment, and wherein a greater distribution of layers with angled fibers is present within the inner segment of the implant. Optionally the angled fibers are positively or negatively angled with regard to longitudinal axis. Optionally the inner segment comprises an inner 50% of the wall thickness. Optionally the inner segment comprises an inner 35% of the wall thickness. Optionally the inner segment comprises an inner 30% of the wall thickness. Optionally the inner segment comprises an inner 25% of the wall thickness.

Optionally the outer segment comprises a greater distribution of layers with the angled fibers. Optionally the outer segment comprises an inner 50% of the wall thickness. Preferably the outer segment comprises an inner 35% of the wall thickness. Optionally the outer segment comprises an inner 30% of the wall thickness. Optionally the outer segment comprises an inner 25% of the wall thickness.

The implant may optionally further comprise a plurality of layers, wherein a distribution of layers with angled fibers is a 10% greater distribution by number of layers or by weight in the inner segment as compared with a remainder of the implant.

Optionally the distribution is 20% greater distribution. Optionally the distribution is 30% greater distribution. Optionally the distribution is 50% greater distribution.

Optionally the implant comprises cannulation and the cannulation is in a diameter range of 0.5-3.5 mm. Optionally the cannulation is in a range of 0.85-1.7 mm.

Optionally an implant diameter is in a range of 2-10 mm. Optionally the diameter is in a range of 3-8 mm. Optionally a cannulation diameter as a percentage of screw diameter is between 10%-50%. Optionally the diameter is 15-45%. Optionally the diameter is 20-40%. Optionally the diameter is 25-35%.

The implant may optionally further comprise a screwdriver driving surface, wherein the driving surface is internal or external to the implant.

Optionally the driving surface comprises one or more of slots, grooves, recesses, or socket. Optionally the driving surface comprises a constant cross section. Optionally the driving surface comprises a variable cross section. Optionally the driving surface comprises a taper cross section.

The implant may optionally further comprise a plurality of chopped fibers at the driving surface, wherein a length of the chopped fibers is less than a length of the driving surface.

The implant may optionally further comprise a plurality of layers, wherein the driving surface comprises at least one layer, wherein the at least one layer comprises a plurality of chopped fibers, wherein a length of the chopped fibers is less than a length of the at least one layer.

The implant may optionally further comprise a single set of threads.

The implant may optionally further comprise multiple sets of threads.

The implant may optionally further comprise a single start.

The implant may optionally further comprise multiple starts.

The implant may optionally further comprise threads having a fixed lead or progressive lead.

The implant may optionally further comprise threads having a fixed pitch or progressive pitch.

The implant may optionally further comprise a constant or a variable outer diameter.

Optionally threading is not continuous throughout the circumference.

Optionally the threads comprise a shape selected from the group consisting of V thread, buttress, reverse buttress, spiral, combination of buttress and reverse, trapezoidal, square or a combination thereof.

Optionally an average depth of the threads is in the range of 0.2-4 mm. Optionally an average pitch is 0.2-7.0 mm.

The implant may optionally further comprise one or more longitudinal grooves breaking in the threads.

Optionally the grooves span the entire length of the screw thread. Optionally the groove spans up to 80% of the length of the screw thread. Optionally the groove is less than 3 mm in width. Optionally the groove is less than 1.5 mm in width. Optionally the groove is less than 1 mm in width.

Optionally the implant comprises cavities or perforations across part or whole surface area. Optionally the cavities diameter is in a range of 0.1-2.5 mm.

The implant may optionally further comprise two or more parts.

The implant may optionally be divided axially, radially or circumferentially.

Optionally the mineral composition is silica-based. Optionally the silica-based mineral compound has at least one oxide composition in at least one of the following mol. % ranges:

$Na_2O$: 11.0-19.0 mol. %
CaO: 8.0-14.0 mol. %
MgO: 1.5-8.0 mol. %
$B_2O_3$: 0.5-3.0 mol. %
$Al_2O_3$: 0-0.8 mol. %
$P_2O_3$: 0.1-0.8 mol. %
$SiO_2$: 65-73 mol. %

Optionally the silica-based mineral compound has at least one oxide composition in at least one of the following mol. % ranges:

$Na_2O$: 12.0-13.0 mol. %
CaO: 8.0-10.0 mol. %
MgO: 7.0-8.0 mol. %
$B_2O_3$: 1.4-2.0 mol. %
$P_2O_3$: 0.5-0.8 mol. %
$SiO_2$: 65-70 mol. %

Optionally density of the biocomposite composition is between 0.5 to 4 $g/cm^3$. Optionally the density is between 1 to 3 $g/cm^3$. Optionally the density is between 1.3-2.5 $g/cm^3$.

Optionally the mineral content is provided by a reinforcing mineral fiber made from the mineral composition. Optionally a diameter of the fiber is in the range of 8-15 μm. Optionally the reinforcing fibers comprise fiber segments inside a polymer matrix, wherein the polymer is biodegradable and wherein the biodegradable polymer is embodied in a biodegradable composite to form the matrix.

Optionally the fibers are embedded in a polymer matrix comprising the biocomposite. Optionally the polymer comprises lactide, glycolide, caprolactone, valerolactone, carbonates (e.g., trimethylene carbonate, tetramethylene carbonate, and the like), dioxanones (e.g., 1,4-dioxanone), δ-valerolactone, 1, dioxepanones) e.g., 1,4-dioxepan-2-one and 1,5-dioxepan-2-one), ethylene glycol, ethylene oxide, esteramides, γ-ydroxyvalerate, β-hydroxypropionate, alpha-hydroxy acid, hydroxybuterates, poly (ortho esters), hydroxy alkanoates, tyrosine carbonates, polyimide carbonates, polyimino carbonates such as poly (bisphenol A-iminocarbonate) and poly (hydroquinone-iminocarbonate, (polyurethanes, polyanhydrides, polymer drugs (e.g., polydiflunisol, polyaspirin, and protein therapeutics), sugars; starch, cellulose and cellulose derivatives, polysaccharides, collagen, chitosan, fibrin, hyaluronic acid, polypeptides, proteins, poly (amino acids), polylactides (PLA), poly-L-lactide (PLLA), poly-DL-lactide (PDLLA); polyglycolide (PGA); copolymers of glycolide, glycolide/trimethylene carbonate copolymers (PGA/TMC); other copolymers of PLA, such as lactide/tetramethylglycolide copolymers, lactide/trimethylene carbonate copolymers, lactide/d-valerolactone copolymers, lactide/ε-caprolactone copolymers, L-lactide/DL-lactide copolymers, glycolide/L-lactide copolymers (PGA/PLLA), polylactide-co-glycolide; terpolymers of PLA, such as lactide/glycolide/trimethylene carbonate terpolymers, lactide/glycolide/ε-caprolactone terpolymers, PLA/polyethylene oxide copolymers; polydepsipeptides; unsymmetrically-3,6-substituted poly-1,4-dioxane-2,5-diones; polyhydroxyalkanoates; such as polyhydroxybutyrates (PHB); PHB/b-hydroxyvalerate copolymers (PHB/PHV); poly-b-hydroxypropionate (PHPA); poly-p-dioxanone (PDS); poly-d-valerolactone-poly-ε-capralactone, poly(ε-caprolactone-DL-lactide) copolymers; methylmethacrylate-N-vinyl pyrrolidone copolymers; polyesteramides; polyesters of oxalic acid; polydihydropyrans; polyalkyl-2-cyanoacrylates; polyurethanes (PU); polyvinylalcohol (PVA); polypeptides; poly-b-malic acid (PMLA): poly-b-alkanbic acids; polycarbonates; polyorthoesters; polyphosphates; poly(ester anhydrides); and mixtures thereof and derivatives, copolymers and mixtures thereof.

Optionally the polymer is selected from the group consisting of PLLA, PDLA, PGA, PLGA, PCL, PLLA-PCL and a combination thereof.

Optionally there is provided a method of treatment for an orthopedic application in a subject in need of treatment thereof, comprising implanting to the subject the medical implant as described herein.

Optionally the implanting to the subject comprises performing structural fixation for a load-bearing purpose within the subject.

Optionally the performing structural fixation comprises performing bone fixation.

The term "biodegradable" as used herein also refers to materials that are resorbable, bioabsorbable or absorbable in the body.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the drawings.

DETAILED DESCRIPTION

Figure 1:
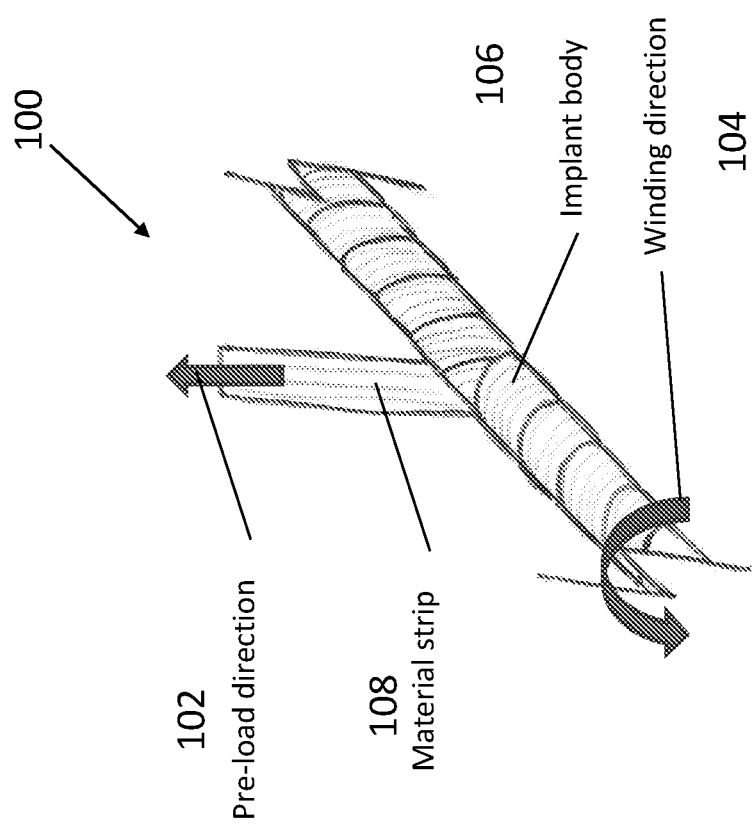
FIG. 1 shows an illustration of an exemplary strip winding process.

The present invention, in at least some embodiments, relates to a biocomposite threaded implant that is reinforced by mineral fibers. Preferably, a weight percentage of a mineral composition within the biocomposite medical implant is in the range of 30-60%, as described in greater detail below. The internal structures and architectures of the implant, in particular the organization and orientation of the fibers within the polymer matrix, provide the implant with beneficial mechanical properties that allow the implant to function effectively in orthopedic fixation. Furthermore, these structures allow the implant to have these mechanical properties while still enabling the ingrowth of bone from surrounding tissues.

The present invention, in at least some embodiments, specifically refers to screws and threaded implants comprised of a biocomposite composition comprising bioabsorbable polymer and reinforcing mineral fibers.

Preferably the biocomposite material composition is comprised of (an optionally bioabsorbable) polymer reinforced by a mineral composition. Preferably the mineral composition reinforcement is provided by a reinforcing fiber made from the mineral composition. As described above, the mineral content of the implant is preferably quite high.

Optionally, the medical implant or part thereof is comprised of a number of biocomposite layers, each layer comprising bioabsorbable polymer reinforced by uni-directional reinforcing fibers. The properties of the implant are optionally and preferably determined according to the layer composition and structure, and the placement of the layers in regard to the device, for example with regard to layer direction. The fibers may optionally remain discrete but optionally some melting of the polymer may occur to bind the layers together.

A biocomposite layer can be defined as a continuous or semi-continuous stratum running through part or all of a medical implant, wherein the layer is comprised of reinforcing fibers that aligned uni-directionally.

Optionally, the directional fiber orientation between adjacent layers within the implant alternates between layers such that each adjacent layer is out of phase (of a different angle) from the layer that is adjacent to it. Preferably, the average or median angle difference between layers is between 15 to 75 degrees, more preferably between 30 to 60 degrees, and most preferably between 40 to 50 degrees.

Preferably, the biocomposite layers within the medical implant are well approximated to each other. More preferably, the distance between layers, as measured by the distance between the last fiber in one layers and the first fiber in the subsequent layer is between 0-200 µm, more preferably between 0-60 µm, 1-40 µm, and most preferably between 2-30 µm. Good approximation of the fibers within a layer to the fibers within the adjacent layer allow each layer to mechanically support the adjacent layer. However, some distance between the layers may be desirable to allow for some polymer to remain between the fibers of adjacent layers and thus adhere the layers together, prevent layer dehiscence under high mechanical load.

Optionally, the fibers are present in the implant in either linear or concentric circular layers. Preferably, each layer is uniform in the orientation of its fibers.

Optionally the number of layers is constant across the implant. Alternatively and optionally the number of layers varies across the implant.

Preferably the layers are of thickness 0.05-0.3 mm and more preferably 0.1 mm to 0.18 mm.

Preferably the thickness of the layers is constant across the implant.

Alternatively the thickness of the layers varies across the screw or implant.

Preferably the layers are 8-40 fibers thick, and more preferably 8-15 fibers thick. Optionally, each layer is comprised of fibers aligned at the longitudinal axis to the implant, at an angle to the longitudinal axis, or at a negative angle to the longitudinal axis.

Optionally, the differently aligned layers are distributed evenly throughout the implant.

Optionally, the diameter of a majority of reinforcing fiber for use with herein reinforced biocomposite medical implant is in the range of 1-100 µm. Preferably, fiber diameter is in the range of 1-20 µm. More preferably, fiber diameter is in the range of 4-16 µm, and most preferably in the range of 8-15 µm.

Optionally, the average diameter of reinforcing fiber for use with herein reinforced biocomposite medical implant is in the range of 1-100 µm. Preferably, fiber diameter is in the range of 1-20 µm. More preferably, fiber diameter is in the range of 4-16 µm, and most preferably in the range of 8-15 µm.

The standard deviation of fiber diameter between fibers within the medical implant is preferably less than 5 µm, more preferably less than 3 µm, and most preferably less than 1.5 µm. Uniformity of fiber diameter is beneficial for consistent properties throughout the implant.

In one embodiment, reinforcing fibers are fiber segments inside the polymer matrix. Preferably such fiber segments are, on average, of length 0.5-20 mm, more preferably the fiber segment length is in the range of 1-15 mm, more preferably in the range of 3-10 and most preferably in the range of 4-8 mm.

Preferably, a majority of reinforcing fiber segments are of length 0.5-20 mm, more preferably the fiber segment length is in the range of 1-15 mm, more preferably in the range of 3-10 and most preferably in the range of 4-8 mm.

Optionally, the reinforcing fibers are continuous fibers. The continuous fibers are preferably longer than 5 mm, more preferably longer than 8 mm, 12 mm, 16 mm, and most preferably longer than 20 mm.

Alternatively, or in addition, the reinforcing fiber length can be defined as a function of implant length wherein at least a portion of the reinforcing fibers, and preferably a majority of the reinforcing fibers, are of a continuous length at least 50% the longitudinal length of the medical implant or medical implant component that is comprised of these fibers. Preferably, the portion or majority of the reinforcing fibers are of continuous length at least 60% of the length of the medical implant, and more preferably at least 75% of the length of the medical implant. Such continuous reinforcing fibers can provide structural reinforcement to a large part of the implant.

Optionally, the distance between adjacent reinforcing fibers within a biocomposite layer is in the range of 0.5-50 µm, preferably the distance between adjacent fibers is in the range of 1-30 µm, more preferably in the range of 1-20 µm, and most preferably in the range of 1-10 µm.

Preferably, the weight percentage of the reinforcing fibers (mineral composition) within the biocomposite medical implant is in the range of 40-90%, more preferably the weight percentage is in the range of 40%-70%, more preferably in the range of 40%-60%, and even more preferably the weight percentage is in the range of 45%-60%.

Preferably, the volume percentage of reinforcing fibers within the biocomposite medical implant is in the range of 30-90%, more preferably the volume percentage is in the range of 40%-70%.

Optionally, a plurality of fibers within the implant are uni-directionally aligned. Optionally, the aligned fiber segments are, on average, of length 5-12 mm.

Preferably, the uni-directionally aligned fibers are aligned in the longitudinal axis of the implant (0° alignments in relation to the longitudinal axis). Preferably, between 10%-100% of fibers are oriented in the longitudinal axis of the implant. More preferably, between 30%-70% of the fibers are so oriented. Most preferably between 40%-60% of the fibers are so oriented.

Optionally, a plurality of fibers are additionally aligned in up to 3 additional directions. Optionally, a plurality of fibers are aligned in a selection of each of the following alignments in relation to the longitudinal axis: 0°, 30°, −30°, 45°, −45°, 90°. Preferably, a plurality of fibers are aligned in a selection of each of the following alignments in relation to the longitudinal axis: 0°, 45°, −45°, 90°. More preferably, a plurality of fibers are aligned in a selection of each of the following alignments in relation to the longitudinal axis: 0°, 45°, −45°.

Optionally and alternatively, fiber segments are arranged amorphously.

While the biocomposite composition within the implant is important in determining the mechanical and bulk properties of the implant, the specific composition and structure that comes into contact with the surface edge of the implant has unique significance in that this composition and structure can greatly affect how surrounding cells and tissue interact with the implant following implantation into the body. For example, the absorbable polymer part of the biocomposite may be hydrophobic in nature such that it will repel surrounding tissues to a certain degree while the mineral reinforcing fiber part of the biocomposite may be hydrophilic in nature and therefore encourage surrounding tissues to attach to the implant or create tissue ingrowth.

In an optional embodiment of the herein invention, the surface presence of one of the compositional components by percentage of surface area is greater than the presence of that component in the bulk composition of the implant by volume percentage. For example, the amount of mineral on the surface might be greater than the amount of polymer, or vice versa. Without wishing to be limited by a single hypothesis, for greater integration with bone, a greater amount of mineral would optionally and preferably be present on the surface. For reduced integration with bone, a greater amount of polymer would optionally and preferably be present on the surface. Preferably, the percentage of surface area composition of one component is more than 10% greater than the percentage of volume percentage of that component in the overall biocomposite implant. More preferably, the percentage is more than 30% greater, and most preferably more than 50% greater.

Optionally, one surface of the medical implant may have a local predominance of one of the biocomposite components while a different surface, or different part of the same surface, may have a local predominance of a different biocomposite component Optionally, mineral content is not present in a majority of the surface area (i.e. a majority of the surface of the implant is covered with a polymer film). Optionally, the surface polymer film is, on average, 0.5-50 µm in thickness, more preferably 5-50 µm and most preferably 10-40 µm.

Optionally, the percentage of fiber exposure at the external surface of the screw or implant will be equal to the percentage of fibers within the screw or implant. Optionally, the percentage of fiber exposure at the surface will be 10% less (as a weight percentage of the total screw/implant) than the percentage of fibers within the screw or implant. Optionally, 20% less or 30% less. Alternatively, 100% less. Optionally the fibers may be exposed in fixed patterns or areas across the implant surface The term external surface of the implant may optionally refer to the external 100 um of the implant, preferably the external 50 um, more preferably the external 30 um, and most preferably the external 15 um.

Preferably, the alignment of a plurality of fibers within the external surface of the implant are at an angle to the longitudinal axis of the implant that is similar to the angle of some or all of the threads of the implant. Similar angle in this context can mean an angle that is within 20 degrees of the angle.

Optionally, the medical implant is a threaded screw or other threaded implant. Preferably, the outer layer of the implant will be directionally aligned such that the direction of the fibers approximates the helix angle of the threading. Preferably, the alignment angle of the fiber direction is within 45 degrees of the helix angle. More preferably, the alignment angle is within 30 degrees, and most preferably the alignment angle is within 15 degrees of the helix angle. Approximating the fiber alignment angle to the helix angle in this manner can improve the robustness of the threading and prevent dehiscence of the reinforcing fibers within the threading.

Bioabsorbable Polymers

In a preferred embodiment of the present invention, the biodegradable composite comprises a bioabsorbable polymer.

The medical implant described herein may be made from any biodegradable polymer. The biodegradable polymer may be a homopolymer or a copolymer, including random copolymer, block copolymer, or graft copolymer. The biodegradable polymer may be a linear polymer, a branched polymer, or a dendrimer. The biodegradable polymers may be of natural or synthetic origin.

Examples of suitable biodegradable polymers include, but are not limited to polymers such as those made from lactide, glycolide, caprolactone, valerolactone, carbonates (e.g., trimethylene carbonate, tetramethylene carbonate, and the like), dioxanones (e.g., 1,4-dioxanone), δ-valerolactone, 1, dioxepanones (e.g., 1,4-dioxepan-2-one and 1,5-dioxepan-2-one), ethylene glycol, ethylene oxide, esteramides, γ-ydroxyvalerate, β-hydroxypropionate, alpha-hydroxy acid, hydroxybuterates, poly (ortho esters), hydroxy alkanoates, tyrosine carbonates, polyimide carbonates, polyimino carbonates such as poly (bisphenol A-iminocarbonate) and poly (hydroquinone-iminocarbonate), polyurethanes, polyanhydrides, polymer drugs (e.g., polydiflunisol polyaspirin, and protein therapeutics) and copolymers and combinations thereof. Suitable natural biodegradable polymers include those made from collagen, chitin, chitosan, cellulose, poly (amino acids), polysaccharides, hyaluronic acid, gut, copolymers and derivatives and combinations thereof.

According to the present invention, the biodegradable polymer may be a copolymer or terpolymer, for example: polylactides (PLA), poly-L-lactide (PLLA), poly-DL-lactide (PDLLA); polyglycolide (PGA); copolymers of glycolide, glycolide/trimethylene carbonate copolymers (PGA/TMC); other copolymers of PLA, such as lactide/tetramethylglycolide copolymers, lactide/trimethylene carbonate copolymers, lactide/d-valerolactone copolymers, lactide/ε-caprolactone copolymers, L-lactide/DL-lactide copolymers, glycolide/L-lactide copolymers (PGA/PLLA), polylactide-co-glycolide; terpolymers of PLA, such as lactide/glycolide/trimethylene carbonate terpolymers, lactide/glycolide/ε-caprolactone terpolymers, PLA/polyethylene oxide copolymers; polydepsipeptides; unsymmetrically-3,6-substituted poly-1,4-dioxane-2,5-diones; polyhydroxyalkanoates; such as polyhydroxybutyrates)PHB); PHB/b-hydroxyvalerate copolymers (PHB/PHV); poly-b-hydroxypropionate (PHPA); poly-p-dioxanone (PDS); poly-d-valerolactone-poly-ε-capralactone, poly(ε-caprolactone-DL-lactide) copolymers; methylmethacrylate-N-vinyl pyrrolidone copolymers; polyesteramides; polyesters of oxalic acid; polydihydropyrans; polyalkyl-2-cyanoacrylates; polyurethanes (PU); polyvinylalcohol (PVA); polypeptides; poly-b-malic acid (PMLA): poly-b-alkanbic acids; polycarbonates; polyorthoesters; polyphosphates; poly(ester anhydrides); and mixtures thereof; and natural polymers, such as sugars; starch, cellulose and cellulose derivatives, polysaccharides, collagen, chitosan, fibrin, hyalyronic acid, polypeptides and proteins. Mixtures of any of the above-mentioned polymers and their various forms may also be used.

Reinforced Bioabsorbable Polymers

According to at least some embodiments of the present invention, the medical implant comprises a reinforced bioabsorbable polymer (i.e. a bioabsorbable composite that includes the previously described polymer and also incorporates a reinforcing filler, generally in fiber form, to increase the mechanical strength of the polymer).

In a more preferred embodiment of the present invention, the reinforced bioabsorbable polymer is a reinforced polymer composition comprised of any of the above-mentioned bioabsorbable polymers and a reinforcing filler, preferably in fiber form. The reinforcing filler may be comprised of organic or inorganic (that is, natural or synthetic) material. Reinforcing filler may be a biodegradable glass, a cellulosic material, a nano-diamond, or any other filler known in the art to increase the mechanical properties of a bioabsorbable polymer. The filler is preferably made from a material or class of material other than the bioabsorbable polymer itself. However, it may also optionally be a fiber of a bioabsorbable polymer itself.

Numerous examples of such reinforced polymer compositions have previously been documented. For example: A biocompatible and resorbable melt derived glass composition where glass fibers can be embedded in a continuous polymer matrix (EP 2 243 749 A1), Biodegradable composite comprising a biodegradable polymer and 20-70 vol % glass fibers (WO2010128039 A1), Resorbable and biocompatible fiber glass that can be embedded in polymer matrix (US 2012/0040002 A1), Biocompatible composite and its use (US 2012/0040015 A1), Absorbable polymer containing poly[succinimide] as a filler (EP0 671 177 B 1).

In a more preferred embodiment of the present invention, the reinforcing filler is bound to the bioabsorbable polymer such that the reinforcing effect is maintained for an extended period. Such an approach has been described in US 2012/0040002 A1 and EP 2243500B1, which discusses a composite material comprising biocompatible glass, a biocompatible matrix polymer and a coupling agent capable of forming covalent bonds.

As noted above, the biodegradable composite and fibers are preferably arranged in the form of biodegradable composite layers, where each layer comprises uni-directionally aligned continuous reinforcement fibers embedded in a polymer matrix comprised of one or more bioabsorbable polymers.

The biodegradable composite layers are preferably comprised of one or more biodegradable composite tapes, where each tape comprises uni-directionally aligned continuous reinforcement fibers embedded in a polymer matrix comprised of one or more bioabsorbable polymers.

The biodegradable composite is preferably embodied in a polymer matrix, which may optionally comprise any of the above polymers. Optionally and preferably, it may comprise a polymer selected from the group consisting of PLLA (poly-L-lactide), PDLLA (poly-DL-lactide), PLDLA, PGA (poly-glycolic acid), PLGA (poly-lactide-glycolic acid), PCL (Polycaprolactone), PLLA-PCL and a combination thereof. If PLLA is used, the matrix preferably comprises at least 30% PLLA, more preferably 50%, and most preferably at least 70% PLLA. If PDLA is used, the matrix preferably comprises at least 5% PDLA, more preferably at least 10%, most preferably at least 20% PDLA.

Preferably, the inherent viscosity (IV) of the polymer matrix (independent of the reinforcement fiber) is in the range of 1.2 to 2.4 dl/g, more preferably in the range of 1.5 to 2.1 dl/g, and most preferably in the range of 1.7 to 1.9 dl/g.

Inherent Viscosity (IV) is a viscometric method for measuring molecular size. IV is based on the flow time of a polymer solution through a narrow capillary relative to the flow time of the pure solvent through the capillary.

Reinforcement Fiber

Preferably, reinforcement fiber is comprised of silica-based mineral compound such that reinforcement fiber comprises a bioresorbable glass fiber, which can also be termed a bioglass fiber composite.

Mineral composition may include beta-tricalcium phosphate, calcium phosphate, calcium sulfate, hydroxyapatite, or a bioresorbable glass (also known as bioglass).

Additional optional glass fiber compositions have been described previously by Lehtonen T J et al. (Acta Biomaterialia 9 (2013) 4868-4877), which is included here by reference in its entirety; such glass fiber compositions may optionally be used in place of or in addition to the above compositions.

Additional optional bioresorbable glass compositions are described in the following patent applications, which are hereby incorporated by reference as if fully set forth herein: Biocompatible composite and its use (WO2010122098); and Resorbable and biocompatible fibre glass compositions and their uses (WO2010122019).

In a more preferred embodiment of the present invention, the reinforcing filler is bound to the bioabsorbable polymer such that the reinforcing effect is maintained for an extended period. Such an approach has been described in US 2012/0040002 A1 and EP 2243500B1, which discusses a composite material comprising biocompatible glass, a biocompatible matrix polymer and a coupling agent capable of forming covalent bonds.

Bioresorbable glass fiber may optionally have oxide compositions in the following mol. % ranges:
$Na_2O$: 11.0-19.0 mol. %
$CaO$: 8.0-14.0 mol. %
$MgO$: 1.5-8.0 mol. %
$B_2O_3$: 0.5-3.0 mol. %
$Al_2O_3$: 0-0.8 mol. %
$P_2O_3$: 0.1-0.8 mol. %
$SiO_2$: 65-73 mol. %
And more preferably in the following mol. % ranges:
$Na_2O$: 12.0-13.0 mol. %
$CaO$: 8.0-10.0 mol. %
$MgO$: 7.0-8.0 mol. %
$B_2O_3$: 1.4-2.0 mol. %
$P_2O_3$: 0.5-0.8 mol. %
$SiO_2$: 65-70 mol. %

Additional optional glass fiber compositions have been described previously by Lehtonen T J et al. (*Acta Biomaterialia* 9 (2013) 4868-4877), which is included here by reference in its entirety; such glass fiber compositions may optionally be used in place of or in addition to the above compositions.

Additional optional bioresorbable glass compositions are described in the following patent applications, which are hereby incorporated by reference as if fully set forth herein: Biocompatible composite and its use (WO2010122098); and Resorbable and biocompatible fibre glass compositions and their uses (WO2010122019).

Threaded Implant Structure

A screw is a non-limiting example of a threaded implant. Threaded implants generally are used for internal bone fixation and there are different designs based on the type of fracture and how the screw will be used. Screws come in different sizes for use with bones of different sizes. Screws can be used alone to hold a fracture, as well as with plates, rods, or nails. After the bone heals, screws may be either left in place or removed.

For the threaded implants of the present invention, at least according to some embodiments, optionally they are provided as a medical implant comprising a biocomposite, the biocomposite comprising a polymer and a plurality of reinforcement fibers. Optionally an average diameter of the fibers is in a range of 1-100 microns. Preferably, the medical implant is threaded with a plurality of threads. Preferably the fibers comprise a plurality of helical fibers and a plurality of longitudinal fibers.

Optionally a weight to weight percent ratio of the helical to the longitudinal fibers is from 90:10 to 10:90, but is preferably from 80:20 to 20:80, and more preferably from 33:66 to 66:33.

Optionally a winding angle of the helical layers is in a range of from 5 to 60 degrees, preferably from 20 degrees to 45 degrees.

The implant threads may be of a constant pitch or of a variable pitch. If of a constant pitch, optionally the pitch angle is in the range of 1 to 45 degrees, optionally in the range of 5 to 20 degrees or alternatively in the range of 20 to 45 degrees.

If of a variable pitch angle, optionally the pitch angle is in the range of 0 to 90 degrees, preferably in the range of 0 to 45 degrees, and more preferably in the range of 20 to 45.

As noted above, the biocomposite is preferably arranged in a plurality of layers, wherein fibers in each layer are discontinuous to an adjacent layer.

Optionally helical fibers in a first layer are wound clockwise while helical fibers in an adjacent layer are wound counterclockwise. Optionally the winding angle is wound toward an area of greater torsional stress of the implant. Optionally an angle between the thread and the angle of the helical fibers is in a range of from 0 to 60 degrees, preferably in the range of 40 to 60 degrees, or optionally in the range of 0 to 20 degrees.

Optionally implant has a longitudinal axis and wherein longitudinal fibers in a first layer have a first angle with respect to the longitudinal axis and longitudinal fibers in a second layer have a second angle with respect to the longitudinal axis.

Optionally the angle range between implant's axis and longitudinal fibers is in the range of −5° to 5°.

Preferably the implant comprises a plurality of helical layers and a plurality of longitudinal layers, wherein the helical and longitudinal layers are each grouped into discrete region of wall thickness of the implant such that they form concentric regions in the implant. Optionally at least one concentric longitudinal fiber region is internal to at least one concentric helical fiber region. Optionally, alternatively or additionally, at least one concentric helical fiber region is external to at least one concentric longitudinal fiber region. Optionally a thickness of the concentric regions is in a range of from 0.2 mm up to 50% of the wall thickness of an implant. Preferably the thickness of the concentric regions is in a range of from 0.2 mm to 4 mm. More preferably the thickness is in a range from 0.2 mm to 2 mm, and most preferably in a range from 0.2 mm to 1 mm.

Optionally a number of helical layers is in a range of from 1 to 15, preferably in the range of 1 to 10, more preferably in the range of 4 to 6, or optionally in the range of 8 to 15. Optionally the diameter of the threaded implant is in the range of 2 to 4 mm and the number of helical layers is in the range of 2-12, preferably 3-8.

Optionally the diameter of the threaded implant is in the range of 3.5 mm to 8 mm and the number of helical layers is in the range of 4-18, preferably 6-14.

Optionally the number of longitudinal layers is in a range of from 1 to 15, preferably in the range of 1 to 10, more preferably in the range of 4-6, or optionally in the range of 1-5.

Optionally the diameter of the threaded implant is in the range of 2 to 4 mm and the number of longitudinal layers is in the range of 1-5, preferably 1-4.

Optionally the diameter of the threaded implant is in the range of 3.5 mm to 8 mm and the number of longitudinal layers is in the range of 1-10, preferably 2-7.

Optionally a number of fibers in the thickness of each helical layer is in a range of from 2-20, preferably in the range from 8-15.

Optionally a number of fibers in the thickness of each longitudinal layer is in a range of from 2-20, preferably in the range from 8-15.

Optionally a number of longitudinal layers is in a range of from 1 to 10, preferably from 4 to 10, and more preferably from 6 to 8.

Optionally an angle between the longitudinal layers is in a range of −5° to 5°.

Optionally the implant features at least one layer of a plurality of layers comprising a plurality of continuous fibers along the layer, and at least one other layer comprising a plurality of chopped fibers, wherein a length of the chopped fibers is less than a length of the at least one other layer. Optionally an average length of chopped fiber is <10% of the length of the implant and preferably <5% of the implant.

Optionally the implant comprises a plurality of different portions, and wherein a concentration of the chopped fibers varies over the plurality of portions of the implant. Preferably the concentration of the chopped fibers varies from 1% to 50% of the biocomposite, preferably 2% to 10% or alternatively 1% to 10% weight per weight percent.

Optionally the implant comprises a head and a body, and wherein the chopped fibers are located at the head for reinforcement.

Optionally the implant comprises a plurality of threads, and wherein the chopped fibers are located at the threads for reinforcement.

Optionally the implant comprises a wall, wherein the wall comprises an inner segment and an outer segment, and wherein a greater distribution of layers with angled fibers is present within the inner segment of the implant. Preferably the angled fibers are positively or negatively angled with regard to longitudinal axis. Optionally and preferably the inner segment comprises an inner 50% of the wall thickness. More preferably, the inner segment comprises an inner 35% of the wall thickness. Most preferably the inner segment comprises an inner 30% of the wall thickness. Also most preferably, the inner segment comprises an inner 25% of the wall thickness.

Optionally the outer segment comprises a greater distribution of layers with the angled fibers. Preferably the outer segment comprises an inner 50% of the wall thickness. More preferably the outer segment comprises an inner 35% of the wall thickness. Most preferably the outer segment comprises an inner 30% of the wall thickness. Also most preferably the outer segment comprises an inner 25% of the wall thickness.

Optionally the implant comprises a plurality of layers, wherein a distribution of layers with angled fibers is a 10% greater distribution by number of layers or by weight in the inner segment as compared with a remainder of the implant. Preferably, the distribution is 20% greater distribution. More preferably, the distribution is 30% greater distribution. Most preferably, the distribution is 50% greater distribution.

Optionally the implant comprises cannulation or is cannulated. If so, optionally the cannulation is in a diameter range of 0.5-3.5 mm. Preferably, the cannulation is in a range of 0.85-1.7 mm. Optionally a cannulation diameter as a percentage of screw diameter is between 10%-50%. Preferably the diameter is 15-45%. More preferably, the diameter is 20-40%. Most preferably, the diameter is 25-35%.

Optionally an implant diameter is in a range of 2-10 mm; preferably the diameter is in a range of 3-8 mm.

Optionally the implant comprises a screwdriver driving surface, wherein the driving surface is internal or external to the implant. Preferably, the driving surface comprises one or more of slots, grooves, recesses, or socket. Optionally and preferably, the driving surface comprises a constant cross section, or alternatively a variable cross section. Optionally the driving surface comprises a taper cross section.

Optionally the implant comprises a plurality of chopped fibers at the driving surface, wherein a length of the chopped fibers is less than a length of the driving surface.

Optionally the implant comprises a plurality of layers, wherein the driving surface comprises at least one layer, wherein the at least one layer comprises a plurality of chopped fibers, wherein a length of the chopped fibers is less than a length of the at least one layer.

Optionally the implant comprises a single set of threads or alternatively comprises multiple sets of threads.

Optionally the implant comprises a single start or alternatively comprises multiple starts.

Optionally the implant comprises threads having a fixed lead or progressive lead, and/or comprises threads having a fixed pitch or progressive pitch.

Optionally the implant comprises a constant or a variable outer diameter.

Optionally threading is not continuous throughout the circumference.

Optionally the threads comprise a shape selected from the group consisting of V thread, buttress, reverse buttress, spiral, combination of buttress and reverse, trapezoidal, square or a combination thereof.

Optionally an average depth of the threads is in the range of 0.2-4 mm.

Optionally an average pitch is 0.2-7.0 mm.

Optionally the implant comprises one or more longitudinal grooves breaking in the threads. Optionally the grooves span the entire length of the screw thread. Alternatively, the groove spans up to 80% of the length of the screw thread.

Optionally the groove is less than 3 mm in width. Preferably the groove is less than 1.5 mm in width. More preferably the groove is less than 1 mm in width.

Optionally the implant comprises cavities or perforations across part or whole surface area. Preferably the cavities diameter is in a range of 0.1-2.5 mm.

Optionally the implant comprises two or more parts.

Optionally the implant is divided axially, radially or circumferentially.

Screws are threaded, though threading can be either complete or partial. Screws can include compression screws, locking screws, and/or cannulated screws. External screw diameter can be as small as 0.5 or 1.0 mm but is generally less than 3.0 mm for smaller bone fixation. Larger bone cortical screws can be up to 5.0 mm and cancellous screws can even reach 7-8 mm. Some screws are self-tapping and others require drilling prior to insertion of the screw. For cannulated screws, a hollow section in the middle is generally larger than 1 mm diameter in order to accommodate guide wires.

Optionally, there is a greater distribution of layers with angled fibers (positively or negatively angled with regard to longitudinal axis) within the outer segment of the implant.

The outer segment can optionally relate to the outer 50% of the wall thickness, preferably the outer 35%, more preferably the outer 30%, more preferably the outer 25% of the wall thickness, and most preferably the other 15% of the wall thickness.

The screwdriver driving surface may be either internal or external to the screw or implant. Screwdriver driving surface may be slots, grooves, recesses, socket, or any other type of screwdriver interface known in the art.

Optionally the screw driving surface may have a constant cross section

Optionally the screw driving surface may have a variable cross section, which is optionally a taper cross section.

The implant may have a single set of threads or multiple sets of threads.

The implant's thread may have a single start or multiple starts.

Threads may have a fixed lead or progressive lead.

Threads may have a fixed pitch or progressive pitch.

The threaded implant may optionally have a constant or a variable outer diameter. Optionally the threading may not be continuous throughout the circumference.

The screw of threaded implant may have cavities or perforations across part or the whole of the surface area. The cavity diameter can be in a range of 0.1-2.5 mm.

Optionally the screw or thread implant may comprise two or more parts. The implant may be divided axially or radially or circumferentially.

The screw may have a flexible feature that allows to maintain preload.

Threads of the screw or implant may be of various shapes including but not limited to V thread, buttress, reverse buttress, spiral, combination of buttress and reverse, trapezoidal, square and a combination or thereof.

The average depth of the threads is optionally in the range of 0.2-4 mm. The average pitch is optionally 0.2-7.0 mm.

Optionally, the threaded implant has one or more longitudinal grooves that makes a break in the threads. Such grooves optionally span the entire length of the screw thread. Optionally, groove spans up to 80% of the length of the screw thread.

The groove is optionally less than 3 mm in width. Preferably, the groove is less than 1.5 mm in width. More preferably, the groove is less than 1 mm in width.

Optionally the layers along the groove are aligned along the axis of the groove.

Optionally the fibers along the groove are aligned with the axis of the groove.

Optionally the fibers along the groove are angularly aligned with the axis of the groove.

There are a number of specific geometrical ratios that may optionally be implemented for ensuring good performance of the reinforced biocomposite threaded implant.

For example, the range of ratios of average thread height to wall thickness in the screw is preferably between 0.2-1.5 more preferably between 0.3-0.9.

Optionally the mineral content in the threading is different than the body of the implant.

Optionally the mineral content is higher. Optionally the mineral content is lower in the threads.

Optionally the mineral directionality is different in the threads. Optionally the fibers in the threads are not continuous while the fibers are continuous in the body of the implant.

Optionally the threads of the implant are distorted upon insertion possibly increasing the grip in the bone.

Optionally the surface roughness of the screw is different on the threads and on the shaft, specifically rougher on the shaft vs the threads.

Optionally the cannulation of the screw is tapered.

Medical screw indications include bone fixation, soft tissue attachment to bone. Screw can be a compression screw or other. Optionally the screws can be locking or non-locking screws.

Optional Additional Features

The below features and embodiments may optionally be combined with any of the above features and embodiments.

Tensile strength of the reinforcement fiber is preferably in the range of 1200-2800 MPa, more preferably in the range of 1600-2400 MPa, and most preferably in the range of 1800-2200 MPa.

Elastic modulus of the reinforcement fiber is preferably in the range of 30-100 GPa, more preferably in the range of 50-80 GPa, and most preferably in the range of 60-70 GPa.

Optionally, a majority of reinforcement fibers aligned to the longitudinal axis of the medical implant are of a length of at least 50% of the total length of the implant, preferably at least 60%, more preferably at least 75%, and most preferably at least 85%.

Preferably, a plurality of reinforcing fibers are oriented at an angle to the longitudinal axis of the screw or implant. More preferably, a plurality of reinforcing fibers are oriented at an angle to the longitudinal axis of the screw or implant and a plurality of reinforcing fibers are oriented at the same negative angle to the longitudinal axis of the screw or implant.

Preferably, the angle is in the range of 30°-90° and the corresponding negative angle is in the range of from −30° to −90°. More preferably, the angle is in the range of 40°-50° and the corresponding negative angle is in the range of from −40° to −50°. Most preferably, the angle is 45° and the corresponding negative angle is −45°.

Preferably, reinforcing fibers comprise a first portion in the range of 10%-45% of fibers at angle and a second portion in the range of 10%-45% of fibers at corresponding negative angle fibers. More preferably, each portion is in the range of 10%-30% and most preferably each portion is in the range of 20%-30%.

Preferably, there are equal portions of fibers at angle and fibers at corresponding negative angle. More preferably, the percentage amount of fibers at angle is within 10% of overall number of fibers of the amount of the corresponding fibers at negative angle. Most preferably the percentage amount is within 5%.

Preferably, the implant preferably comprises between 2-20 composite tape layers, more preferably between 2-10 layers, and most preferably between 2-6 layers; wherein each layer may be aligned in a different direction or some of the layers may be aligned in the same direction as the other layers. However as noted above, tape is not necessarily a feature of the layers, which may be comprised of a plurality of fibers.

Preferably, the maximum angle between fibers in at least some of the layers is greater than the angle between the fibers in each layer and the longitudinal axis. For example, one layer of reinforcing fibers may be aligned and a right diagonal to the longitudinal axis while another layer may be aligned at a left diagonal to the longitudinal axis.

Compatibilizer

Optionally and preferably, the composite composition additionally includes a compatibilizer, which for example be such an agent as described in WO2010122098, hereby incorporated by reference as if fully set forth herein.

Biodegradable Composite Alternative Forms

Alternatively, biodegradable composite may comprise composite strands comprising continuous reinforcement fibers or fiber bundles impregnated with bioabsorbable polymer. Preferably, strands are less than 1 cm in diameter. More preferably, strands are less than 8 mm, less than 5 mm, less than 3 mm, or less than 2 mm in diameter.

Alternatively, biodegradable composite may comprise a woven mesh of continuous reinforcement fibers wherein woven mesh is pre-impregnated with bioabsorbable polymer or woven mesh is comprised of reinforcement fibers and subsequently impregnated with bioabsorbable polymer.

Preferably, biodegradable composite mesh layer is less than 1 cm in thickness. More preferably, impregnated mesh is less than 8 mm, less than 5 mm, less than 3 mm, or less than 2 mm in thickness.

Mineral Content

The present invention, in at least some embodiments, further overcomes the limitations of previous biocomposite medical implants by providing medical implants comprised of a biocomposite material composition with a high percentage of mineral content and yet with superior mechanical properties. Preferably the mineral composition is provided by a reinforcing fiber made from the mineral composition.

According to some embodiments, preferably, the weight percentage of the mineral composition within the biocomposite medical implant is in the range of 40-90%, more preferably the weight percentage is in the range of 40%-70%, and even more preferably the weight percentage is in the range of 45%-60%. As noted above, optionally and preferably a weight percentage of a mineral composition within the biocomposite medical implant is in the range of 30-60%.

Optionally and preferably, the fiber-reinforced biodegradable composite within the implant has a flexural modulus exceeding 5 GPa and flexural strength exceeding 80 MPa.

Preferably, the fiber-reinforced biodegradable composite within the implant has flexural strength in range of 150-800 MPa, more preferably 150-400 MPa. Elastic modulus is preferably in range of 5-27 GPa, more preferably 10-27 GPa.

Preferably, the fiber-reinforced composite within the implant has strength retention of Elastic Modulus above 10 GPa after 8 weeks implantation and flexural strength above 150 MPa after 8 weeks.

According to the present invention, in at least some embodiments, the biodegradable polymer may be a copolymer or terpolymer, for example: polylactides (PLA), poly-L-lactide (PLLA), poly-DL-lactide (PDLLA); polyglycolide (PGA); copolymers of glycolide, glycolide/trimethylene carbonate copolymers (PGA/TMC); other copolymers of PLA, such as lactide/tetramethylglycolide copolymers, lactide/trimethylene carbonate copolymers, lactide/d-valerolactone copolymers, lactide/ε-caprolactone copolymers, L-lactide/DL-lactide copolymers, glycolide/L-lactide copolymers (PGA/PLLA), polylactide-co-glycolide; terpolymers of PLA, such as lactide/glycolide/trimethylene carbonate terpolymers, lactide/glycolide/ε-caprolactone terpolymers, PLA/polyethylene oxide copolymers; polydepsipeptides; unsymmetrically-3,6-substituted poly-1,4-dioxane-2,5-diones; polyhydroxyalkanoates; such as polyhydroxybutyrates)PHB); PHB/b-hydroxyvalerate copolymers (PHB/PHV); poly-b-hydroxypropionate (PHPA); poly-p-dioxanone (PDS); poly-d-valerolactone-poly-ε-capralactone, poly(c-caprolactone-DL-lactide) copolymers; methylmethacrylate-N-vinyl pyrrolidone copolymers; polyesteramides; polyesters of oxalic acid; polydihydropyrans; polyalkyl-2-cyanoacrylates; polyurethanes (PU); polyvinyl alcohol (PVA); polypeptides; poly-b-malic acid (PMLA): poly-b-alkanbic acids; polycarbonates; polyorthoesters; polyphosphates; poly(ester anhydrides); and mixtures thereof; and natural polymers, such as sugars; starch, cellulose and cellulose derivatives, polysaccharides, collagen, chitosan, fibrin, hyalyronic acid, polypeptides and proteins. Mixtures of any of the above-mentioned polymers and their various forms may also be used.

The biodegradable composite is preferably embodied in a polymer matrix, which may optionally comprise any of the above polymers. Optionally and preferably, it may comprise a polymer selected from the group consisting of PLLA (poly-L-lactide), PDLLA (poly-DL-lactide), PLDLA, PGA (poly-glycolic acid), PLGA (poly-lactide-glycolic acid), PCL (Polycaprolactone), PLLA-PCL and a combination thereof. If PLLA is used, the matrix preferably comprises at least 30% PLLA, more preferably 50%, and most preferably at least 70% PLLA. If PDLA is used, the matrix preferably comprises at least 5% PDLA, more preferably at least 10%, most preferably at least 20% PDLA.

Preferably, the inherent viscosity (IV) of the polymer matrix (independent of the reinforcement fiber) is in the range of 1.2 to 2.4 dl/g, more preferably in the range of 1.5 to 2.1 dl/g, and most preferably in the range of 1.7 to 1.9 dl/g.

Inherent Viscosity (IV) is a viscometric method for measuring molecular size. IV is based on the flow time of a polymer solution through a narrow capillary relative to the flow time of the pure solvent through the capillary.

Mineral composition may optionally include beta-tricalcium phosphate, calcium phosphate, calcium sulfate, hydroxyapatite, or a bioresorbable glass (also known as bioglass).

Bioresorbable glass fiber may optionally have oxide compositions in the following mol. % ranges:

Na2O: 11.0-19.0 mol %.
CaO: 8.0-14.0 mol %.
MgO: 1.5-8.0 mol %.
B2O3: 0.5-3.0 mol %.
Al2O3: 0-0.8 mol %.
P2O3: 0.1-0.8 mol %.
SiO2: 65-73 mol %.

And more preferably in the following mol. % ranges:

Na2O: 12.0-13.0 mol %.
CaO: 8.0-10.0 mol %.
MgO: 7.0-8.0 mol %.
B2O3: 1.4-2.0 mol %.
P2O3: 0.5-0.8 mol %.
SiO2: 65-70 mol %.

Additional optional glass fiber compositions have been described previously by Lehtonen T J et al. (Acta Biomaterialia 9 (2013) 4868-4877), which is included here by reference in its entirety; such glass fiber compositions may optionally be used in place of or in addition to the above compositions.

Additional optional bioresorbable glass compositions are described in the following patent applications, which are hereby incorporated by reference as if fully set forth herein, which are owned in common with the instant application and which have inventor(s) in common: Biocompatible composite and its use (WO2010122098); and Resorbable and biocompatible fibre glass compositions and their uses (WO2010122019).

In a more preferred embodiment of the present invention, the reinforcing filler is bound to the bioabsorbable polymer such that the reinforcing effect is maintained for an extended period. Such an approach has been described in US 2012/0040002 A1 and EP 2243500B1, which discusses a composite material comprising biocompatible glass, a biocompatible matrix polymer and a coupling agent capable of forming covalent bonds.

Medical Implant Composite Structure

The average wall thickness in the implant is preferably in the range of 0.2 to 10 mm, more preferably in the range of 0.4 to 5 mm, more preferably in the range of 0.5 to 2 mm, and most preferably in the range of 0.5 to 1.5 mm.

The implant preferably comprises between 2-30 composite tape layers, more preferably between 3-12 layers, and most preferably between 2-6 layers.

Optionally, implant may comprise reinforcing ribs, gussets, or struts.

Rib base thickness is preferably less than 100% of the adjoining wall thickness. More preferably, thickness is less than 85%, and most preferably less than 75%. Rib base thickness is preferably more than 20% of adjoining wall thickness, more preferably more than 30%, and most preferably more than 50% of adjoining wall thickness.

Preferably, rib height is at least 2.0 times the adjoining wall thickness, more preferably at least 3.0 times the wall thickness.

Draft angle of reinforcing ribs is preferably between 0.2-0.8°, more preferably between 0.4-0.6°.

Preferably, distance between ribs is at least 2 times adjoining wall thickness. More preferably, at least 3 times adjoining wall thickness.

Preferably, reinforcing rib or other element increases bending stiffness of implant by at least 20% without increasing compressive or tensile stiffness by more than 10%.

Optionally, ribs along one axis, for example the longitudinal axis of the implant, are taller than the ribs along the perpendicular axis, for example the latitudinal axis of the implant, in order to facilitate easier insertion of the implant.

Optionally, the implant may comprise one or more bosses to accommodate screw insertion. Preferably, the boss is between 2-3 times the screw diameter for self-tapping screw applications. Boss may additionally include supportive gusses or ribs.

Optionally, one or more sides of implant may be textured.

Optionally, implant may contain continuous fibers aligned in a circular arrangement around holes, such as screw or pin holes, within the implant.

Perforated Implant Part Walls

In some medical implants, it is desirable for there to be cellular or tissue ingrowth through the implant so as to strengthen the incorporation of the implant into the tissue and to increase compliance of the implant in physiological function. In order to further promote such ingrowth, it is beneficial to have gaps or holes in the walls of the herein described medical implant.

Preferably, if present, such perforations in implant walls comprise at least 10% of the surface area of the implant, more preferably at least 20%, at least 30%, at least 40%, or at least 50% of the surface area of the implant.

In one optional embodiment of the present invention, the implant is a screw and the fenestrations of the threading contain perforation.

In one embodiment of the present invention, the implant contains perforations between composite tapes or between the reinforcement fibers within composite tapes making up the implant.

In a preferred embodiment, a majority of perforations are between reinforcement fibers and do not penetrate reinforcement fibers.

Framework of Continuous Fiber Reinforced Structure with Non-Reinforced Surrounding Material Whereas continuous fiber reinforced bioabsorbable composite structures provide the optimal mechanical strength and stiffness to a medical implant, it may also be beneficial in certain cases to have additional features or layers in the medical implant that cannot be made from continuous fiber reinforced composite tapes. In such cases, the mechanical strength of the continuous fiber reinforced bioabsorbable composite structures can be incorporated into the implant but additional sections or layers of non-reinforced polymer may be added to improve or customize the implant. These sections or layers are preferably added to the implant either by overmolding onto the structure or by 3-D printing onto the structure.

In one embodiment of the present invention, medical implant comprises a structural support comprised of a continuous fiber-reinforced bioabsorbable composite material and additionally comprises a section or layer comprised of non-reinforced polymer material.

Optionally the second layer functions as a bone interface layer comprised of a non-reinforced absorbable polymer material. Also optionally the structural support and non-reinforced polymer section are each fabricated using a different production technique. Also optionally the structural support is fabricated by machining, compression molding, or composite flow molding and the interface layer is fabricated by injection molding or 3D printing; optionally the interface layer is fabricated on top of the prefabricated structural support.

Optionally the non-reinforced polymer section is a bone interface layer and dimensions of the interface layer are partially or entirely determined by the bone geometry of a specific patient or patient population.

Optionally the bone geometry of patient or patient population is determined by measuring through imaging technique such as X-Ray, CT, MRI.

Optionally the elastic modulus and/or flexural strength of structural support is at least 20% greater than that of the non-reinforced polymer section.

Optionally, continuous-fiber reinforced composite material in implant is coated with a polymer resin wherein the polymer resin on fiber in the composite material has a higher or lower melting temp than the flowable matrix resin; or polymer resin on fiber has slower or faster degradation rate than flowable matrix resin; or polymer resin on fiber is more hydrophobic or more hydrophilic than flowable matrix resin In an optional embodiment, an additional section or layer is comprised of a reinforced polymer but where polymer is reinforced by non-continuous fibers, preferably fibers less than 10 mm in length, and more preferably less than 5 mm in length.

In an optional embodiment, an additional section or layer of non-reinforced or non-continuous fiber reinforced polymer additional comprises an additive.

Optionally, additive comprises an osteoconductive material or combination of osteoconductive materials such as beta tricalcium phosphate, calcium phosphate, hydroxyapatite, decellularized bone.

Optionally, the additive comprises an anti-microbial agent or bone inducing agent.

Production Method

Continuous-fiber reinforced bioabsorbable implants may optionally be produced using any method known in the art. Methods can include compression molding, injection molding, extrusion, machining, or any combination of these methods.

Preferably, moisture content of implant following production is less than 50%, more preferably less than 1%, even more preferably less than 0.4%, 0.2%.

Low moisture content is important so as to avoid degradation of the implant during storage.

Preferably, residual monomer content in implant following production is less than 3%, preferably less than 2%, and more preferably less than 1%.

Without wishing to be limited by a single hypothesis, where mineral content is high relative to biocomposite implants, it is particularly important that the polymer component be predominantly comprised of polymer, with very low monomer component, since the monomer component does not contribute to the mechanical function of the implant.

Implant Contact with Surrounding Tissue

In an optional embodiment of the present invention, less than 100% of implant surface area is in contact with surrounding tissue. This may be clinically desirable for several reasons:

1. Reduced friction with surrounding tissue upon insertion, easing insertion
2. Reduced bone contact can reduce interference to bone surface blood flow In a preferred embodiment, implant contains surface protrusion elements of at least 0.1 mm in height and less than 2 mm in height that come into contact with tissue surrounding implant.

Preferably, total percentage of surface area of implant that comes into contact with surrounding tissue is less than 80%, more preferably less than 60%, 50%, 40%, 30%.

Fabrication of the Implant

Any of the above-described bioabsorbable polymers or reinforced bioabsorbable polymers may be fabricated into any desired physical form for use with the present invention. The polymeric substrate may be fabricated for example, by compression molding, casting, injection molding, pultrusion, extrusion, filament winding, composite flow molding (CFM), machining, or any other fabrication technique known to those skilled in the art. The polymer may be made into any shape, such as, for example, a plate, screw, nail, fiber, sheet, rod, staple, clip, needle, tube, foam, or any other configuration suitable for a medical device.

Load-Bearing Mechanical Strength

The herein invention particularly relates to bioabsorbable composite materials that can be used in medical applications that require high strength and a stiffness compared to the stiffness of bone. These medical applications require the medical implant to bear all or part of the load applied by or to the body and can therefore be referred to generally as "load-bearing" applications. These include fracture fixation, tendon reattachment, joint replacement, spinal fixation, and spinal cages.

The flexural strength preferred from the herein described load-bearing medical implant is at least 100 MPa, preferably above 400 MPa, more preferably above 600 MPa, and even more preferably above 800 MPa. The Elastic Modulus (or Young's Modulus) of the bioabsorbable composite for use with herein invention is preferably at least 6 GPa, more preferably above 15 GPa, and even more preferably above 20 GPa but not exceeding 100 GPa and preferably not exceeding 60 GPa.

Sustained Mechanical Strength

There is a need for the bioabsorbable load-bearing medical implants of the herein invention to maintain their mechanical properties (high strength and stiffness) for an extended period to allow for sufficient bone healing. The strength and stiffness preferably remains above the strength and stiffness of cortical bone, approximately 150-250 MPa and 15-25 GPa respectively, for a period of at least 3 months, preferably at least 6 months, and even more preferably for at least 9 months in vivo (i.e. in a physiological environment).

More preferably, the flexural strength remains above 400 MPa and even more preferably remains above 600 MPa.

In another embodiment of the present invention, the mechanical strength degradation rate of the medical implant approximates the material degradation rate of the implant, as measured by weight loss of the biodegradable composite.

In a preferred embodiment, the implant retains greater than 50% of its mechanical strength after 3 months of implantation while greater than 50% of material degradation and hence weight loss occurs within 12 months of implantation.

In a preferred embodiment, the implant retains greater than 70% of its mechanical strength after 3 months of implantation while greater than 70% of material degradation and hence weight loss occurs within 12 months of implantation.

In a preferred embodiment, the implant retains greater than 50% of its mechanical strength after 6 months of implantation while greater than 50% of material degradation and hence weight loss occurs within 9 months of implantation.

In a preferred embodiment, the implant retains greater than 70% of its mechanical strength after 6 months of implantation while greater than 70% of material degradation and hence weight loss occurs within 9 months of implantation.

The mechanical strength degradation and material degradation (weight loss) rates of the medical implant can be measured after in vivo implantation or after in vitro simulated implantation. In the case of in vitro simulated implantation, the simulation may be performed in real time or according to accelerated degradation standards.

"Biodegradable" as used herein is a generalized term that includes materials, for example polymers, which break down due to degradation with dispersion in vivo. The decrease in mass of the biodegradable material within the body may be the result of a passive process, which is catalyzed by the physicochemical conditions (e.g. humidity, pH value) within the host tissue. In a preferred embodiment of biodegradable, the decrease in mass of the biodegradable material within the body may also be eliminated through natural pathways either because of simple filtration of degradation by-products or after the material's metabolism ("Bioresorption" or "Bioabsorption"). In either case, the decrease in mass may result in a partial or total elimination of the initial foreign material. In a preferred embodiment, the biodegradable composite comprises a biodegradable polymer that undergoes a chain cleavage due to macromolecular degradation in an aqueous environment.

A polymer is "absorbable" within the meaning of this invention if it is capable of breaking down into small, non-toxic segments which can be metabolized or eliminated from the body without harm. Generally, absorbable polymers swell, hydrolyze, and degrade upon exposure to bodily tissue, resulting in a significant weight loss. The hydrolysis reaction may be enzymatically catalyzed in some cases. Complete bioabsorption, i.e. complete weight loss, may take some time, although preferably complete bioabsorption occurs within 24 months, most preferably within 12 months.

The term "polymer degradation" means a decrease in the molecular weight of the respective polymer. With respect to the polymers, which are preferably used within the scope of the present invention the degradation is induced by free water due to the cleavage of ester bonds. The degradation of the polymers as for example used in the biomaterial as described in the examples follows the principle of bulk erosion. Thereby a continuous decrease in molecular weight precedes a highly pronounced mass loss. The mass loss is attributed to the solubility of the degradation products. Methods for determination of water induced polymer degradation are well known in the art such as titration of the degradation products, viscometry, differential scanning calorimetry (DSC).

The term "Biocomposite" as used herein is a composite material formed by a matrix and a reinforcement of fibers wherein both the matrix and fibers are biocompatible and optionally bioabsorbable. In most cases, the matrix is a polymer resin, and more specifically a synthetic bioabsorbable polymer. The fibers are optionally and preferably of a different class of material (i.e. not a synthetic bioabsorbable polymer), and may optionally comprise mineral, ceramic, cellulosic, or other type of material.

Clinical Applications

The medical implants discussed herein are generally used for bone fracture reduction and fixation to restore anatomical relationships. Such fixation optionally and preferably includes one or more, and more preferably all, of stable fixation, preservation of blood supply to the bone and surrounding soft tissue, and early, active mobilization of the part and patient.

There are several exemplary, illustrative, non-limiting types of bone fixation implants for which the materials and concepts described according to at least some embodiments of the present invention may be relevant, as follows:

Any of the above-described bone fixation implants may optionally be used to fixate various fracture types including but not limited to comminuted fractures, segmental fractures, non-union fractures, fractures with bone loss, proximal and distal fractures, diaphyseal fractures, osteotomy sites, etc.

EXAMPLE 1: Helical Compression Screw Manufacturing Method

Compression screws (CS) were produced by winding strips of biomaterial composite tape around a mandrel.

Material composite was comprised of PLDLA 70/30 polymer reinforced with 47% w/w continuous mineral fibers. Mineral fibers composition was approximately $Na_2O$ 14%, MgO 5.4%, CaO 9%, $B_2O_3$ 2.3%, $P_2O_5$ 1.5%, and $SiO_2$ 67.8% w/w.

Each strip in this example has the following dimensions: 2 mm width, 300 mm length and 0.2 mm thickness. Quantity of pre-cut strips is such that their total weight is as a weight of a final implant plus 30% spare to compensate for material loss due to flashes. In this example the material weighed precisely 0.2 grams. In this example, there were 3 full strips and one strip cut in half wound on a central mandrel to get between seven and eight layers along the thickness of the screw length.

The first pre-cut strip of the material is fixed to the mandrel at an angle of 20° relative to a plane perpendicular to CS axis. The strip is heated with a stream of hot air at 300° C. in order to facilitate bending. At the same time, the mandrel starts to rotate in counter-clockwise (CCW) direction (if viewed from a driver chuck) at a rate of 5-10 RPM and the strip is being wound. During the winding process, the strip is pre-loaded with force of about 200 grams in order to tighten the winding coils on the mandrel. The angle between the material strip and the mandrel remains constant, as well as the pitch of the winding. When the material strip reaches mandrel end, the winding begins in the opposite direction while the pitch and driver speed remain constant. When the material strip ends, a new strip is hot-welded with an air blower to the already wound material at the same spot and the process continues.

When all the strips are wound on the mandrel, the mandrel is inserted into the mold. The mold is heated to 100-130° C. in a hot press and then the pressure of about 1150 bars is applied. The mold stays under pressure for 10 minutes while maintaining the heat in the same range. After that the mold is cooled to 30-37° C. and removed from a press. The implant is removed from a mold and continues to further processing.

TABLE 1

| Implant performance test results: | | |
| --- | --- | --- |
| Test description | Testing method | Result value |
| Bending strength | 3-point-bending as per ASTM D790 | 194 mPa |
| Pull-out force | per ASTM F2502 | 144N |
| Driving torque | per ASTM F2502 | 16N*cm |
| Maximal torque | per ASTM F2502 | 54N*cm |

FIG. 1 shows an illustration of an exemplary strip winding process used with regard to Example 1. As shown, in a process 100, a preload direction 102 of the winding material is shown. There is a tension applied on the tape during winding. Preload is an initial stress that results from the tension applied in the direction of the winding. The winding direction 104 is also shown. The material strip 108 is wound onto the implant body 106, in the winding direction 104.

Figure 2A:
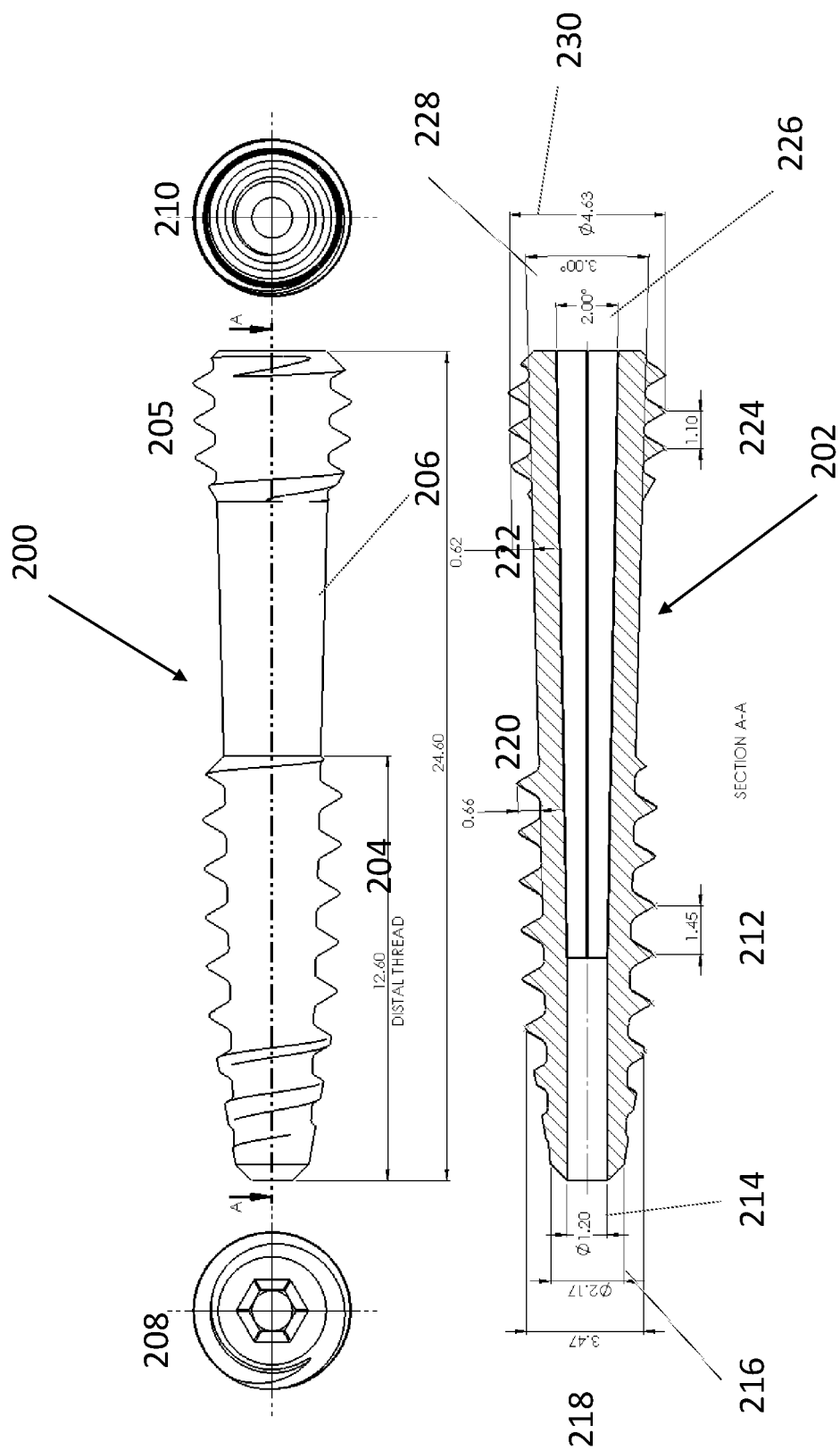
FIGS. 2A and 2B show schematic diagrams of an exemplary screw.
Figure 2B:
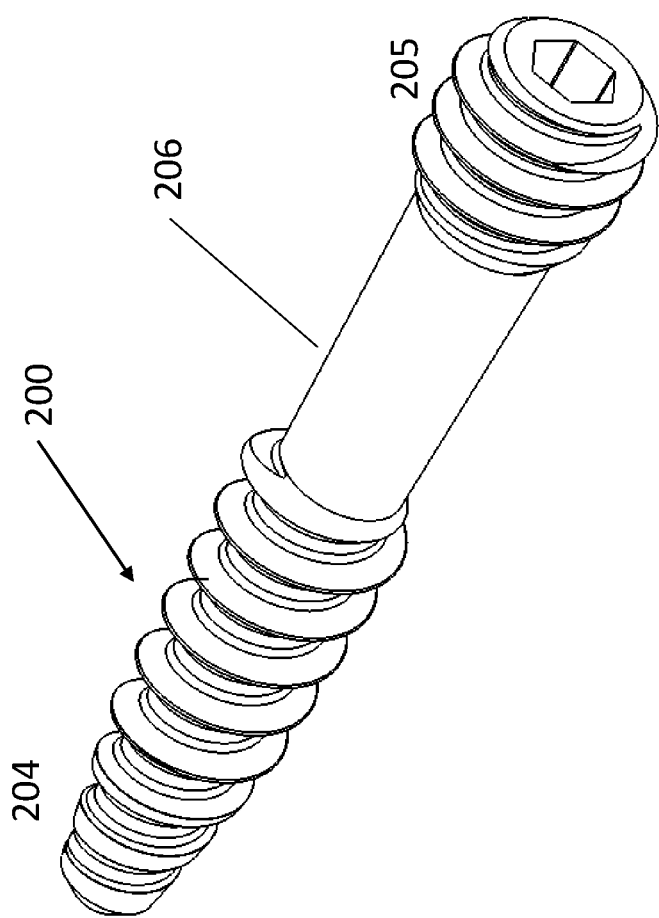

FIGS. 2A and 2B show schematic diagrams of an exemplary screw. As shown in FIG. 2A, a two-dimensional schematic screw 200 is shown (top). FIG. 2A also shows a cross-section 202, through A-A as shown (bottom). Turning back to screw 200, screw 200 features a plurality of distal threads 204, with an exemplary, non-limiting length of 12.60 mm. Screw 200 also features a plurality of proximal threads 205 and a shaft 206. A length of screw 200 is preferably shown, in this non-limiting example, as 24.60 mm.

The bottom and upper view of a typical screw 208 and 210 are also shown.

Turning now to screw cross-section 202, a distance between two distal threads 212 is shown in this non-limiting example to be 1.45 mm. An inner tip 214 has a width in this non-limiting example of 1.20 mm. An outer tip 216 has a width in this non-limiting example of 1.27 mm. A widest section of the distal threads, shown as 218, has a width in this non-limiting example of 3.47 mm. A distance 220 is preferably 0.6 mm, while a distance 222 is preferably 0.67 mm. in this non-limiting example; these distances relate to the thread teeth height and pitch. A distance between two proximal threads 224 is shown in this non-limiting example to be 1.10 mm.

An inner shaft 226 is shown in this non-limiting example to have a width of 2.00 mm. An outer shaft 228 is shown in this non-limiting example to have a width of 3.00 mm. An outermost width from proximal thread to thread is shown in this non-limiting example to be 4.63 mm.

FIG. 2B shows screw 200 in three dimensional perspective, showing again distal threads 204, proximal threads 205 and shaft 206.

Figure 3:
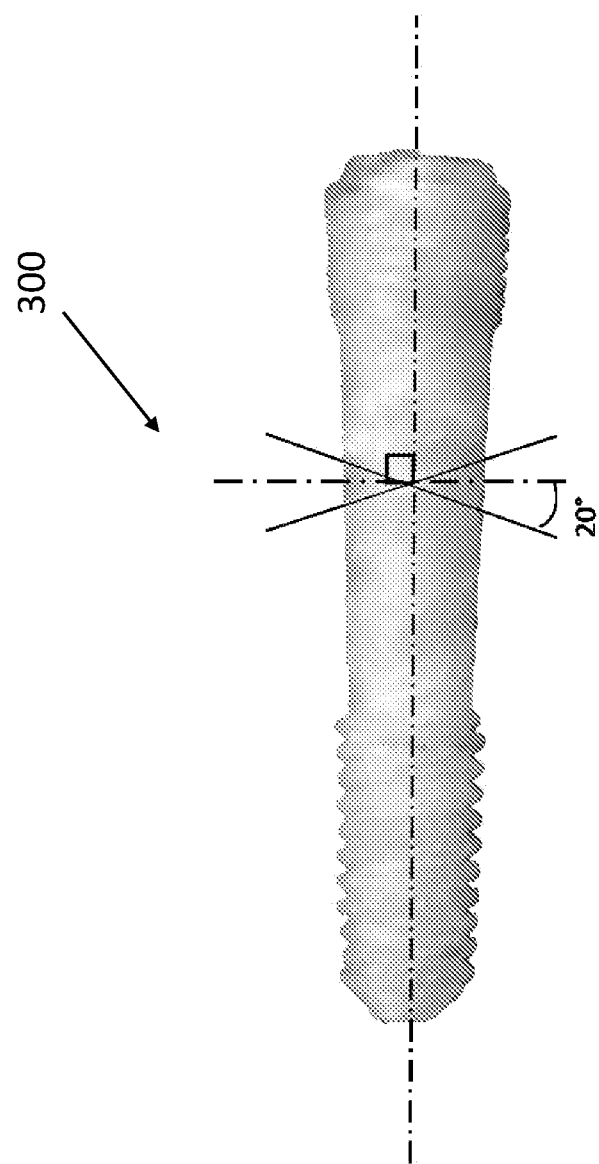
FIG. 3 shows an image of an implant with slightly different design.

FIG. 3 shows an image of an implant with slightly different design; some non-limiting examples of the differences include different diameters, different thread to diameter ratio and different winding angles. Wound fibers are clearly visible at an angle of ~20° relative to a plane perpendicular to implant axis in a screw 300.

EXAMPLE 2: Compression Screw with Straight Fibers Manufacturing Method

Figure 5:
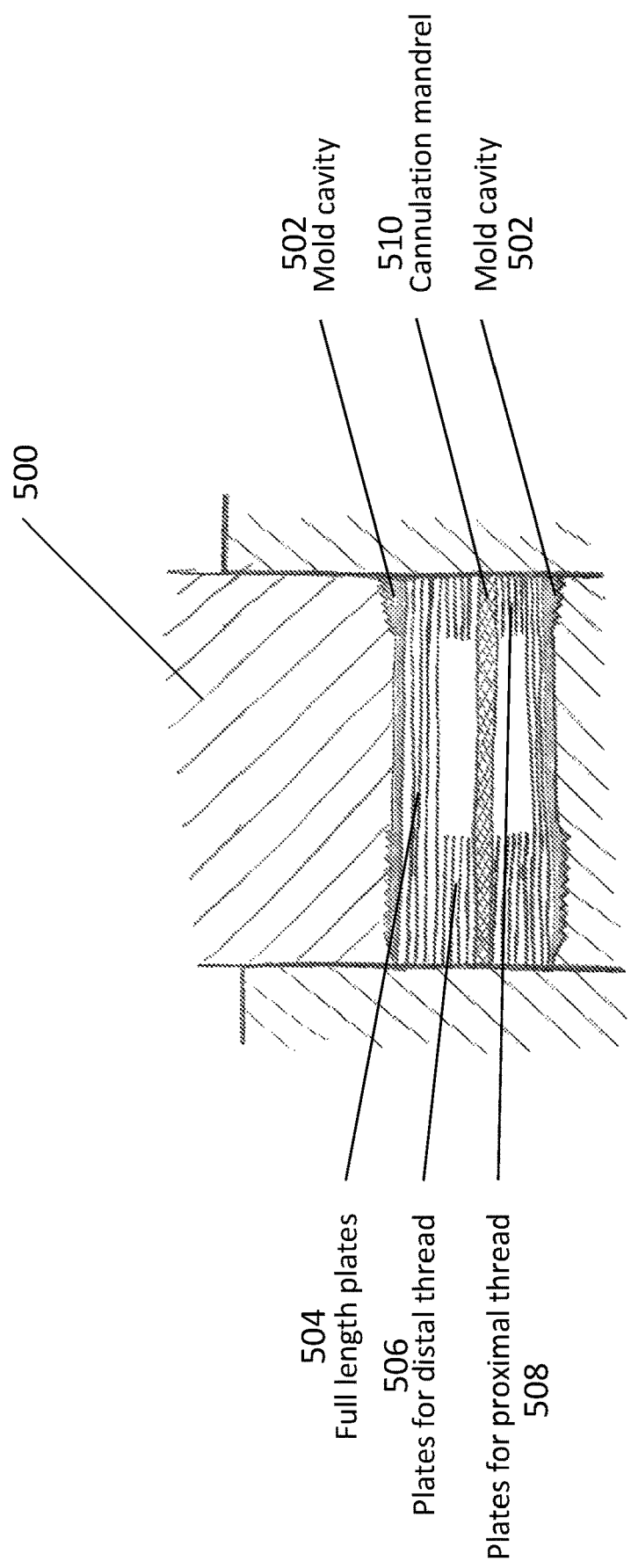
FIG. 5 is an illustration of material loading into a mold with plates of different lengths.

Manufacturing of a compression screw (CS) by with straight parallel fibers begins with material preparation. Majority of the plates of the raw material are cut to a length of an implant with original width and thickness. In this example the plates had the following dimensions: 40 mm length, 13 mm width and 0.2 mm thickness. Additional shorter plates were prepared in order to increase fibers concentration in a thread region. Those plates had same thickness and width but had a length of 15 mm for a distal thread and 5 mm for the proximal thread. Quantity of pre-cut plates is such that their total weight is as a weight of a final implant plus 30% spare to compensate for material loss due to flashes: 0.024 grams for 5 mm plates, 0.034 grams for 15 mm plates and 0.312 grams for full length plates (40 mm). In this example the material weighted precisely 0.37 grams and there were eight full length plates, four 5 mm plates and two 15 mm plates stacked one on top of the other in the arrangement that is illustrated in FIG. 5. Thus, there were seven layers in total in a proximal thread region (four full length+two 5 mm+one 15 mm), 4 layers in total in a shaft region (4 full length) and 5 layers in a distal thread region (four full length+one 15 mm).

Next, pre-cut plates are loaded into the mold and the mold is inserted into the press. The short plates are the first to go in, each type placed in the exact location: 15 mm plates over a distal thread cavity, 5 mm plates over a proximal thread cavity and the full-length plates were placed over them to fill the whole implant cavity in a mold. The mold is heated to 100-130° C. and then the pressure of about 1150 bars is applied. The mold stays under pressure for 10 minutes while maintaining the heat in the same range. After that the mold is cooled to 30-37° C. and removed from a press. The implant is removed from a mold and continues to further processing.

TABLE 2 implant test results

| Test description | Testing method | Result value |
| --- | --- | --- |
| Bending strength | 3-point-bending as per ASTM D790 | 578 mPa |
| Pull-out force | per ASTM F2502 | 200N |
| Driving torque | per ASTM F2502 | 14N*cm |
| Maximal torque | per ASTM F2502 | 14N*cm |

Figure 4A:
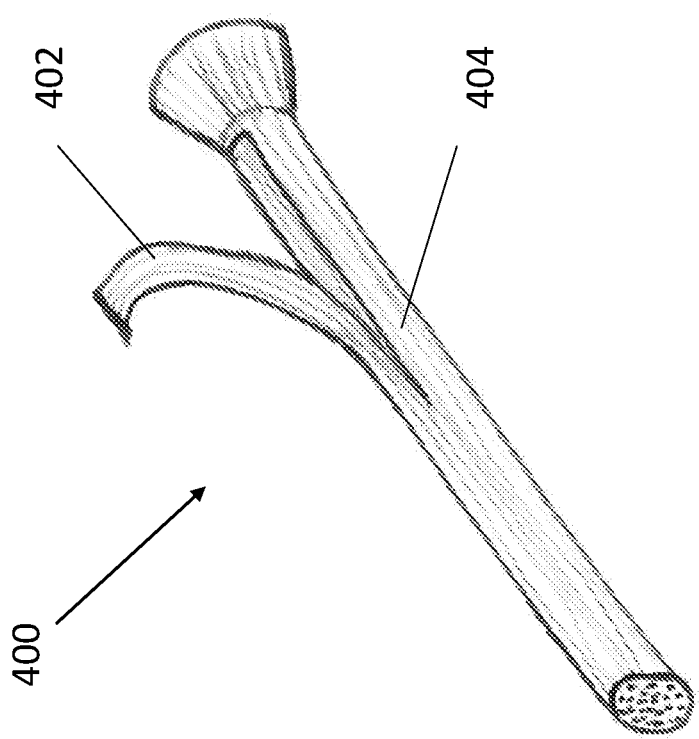
FIGS. 4A and 4B are illustrations of exemplary implants with all straight fibers oriented in same direction parallel to CS axis.
Figure 4B:
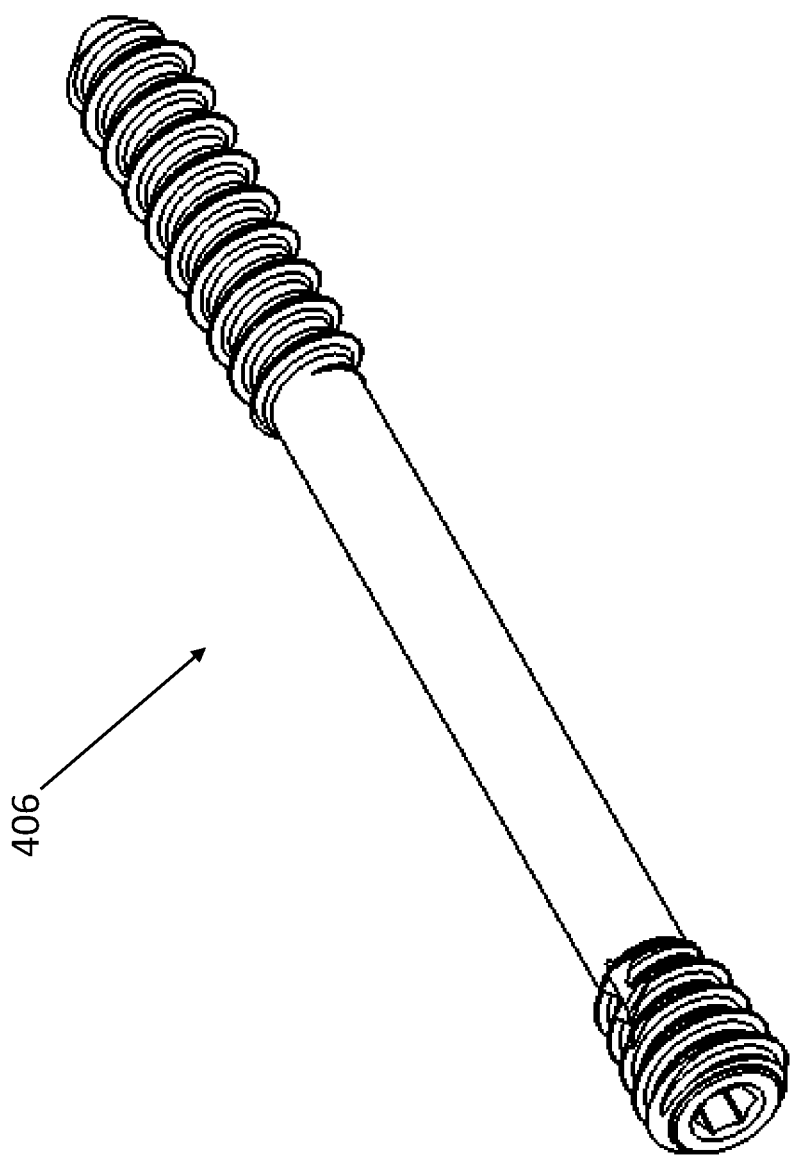

FIGS. 4A and 4B are illustrations of exemplary implants with all straight fibers oriented in same direction parallel to CS axis. FIG. 4A depicts a schematic fiber orientation in an implant 400, with a section 402 peeled away to show all of the fibers 404 with the same orientation parallel to the axis. FIG. 4B depicts the actual implant model 406.

FIG. 5 is an illustration of material loading into a mold with plates of different lengths. A mold 500 features a mold cavity 502. A plurality of full length plates 504 are loaded into mold cavity 502, as are distal thread plates 506 and proximal thread plates 508. All of the plates are preferably distributed evenly on both sides of a mandrel 510.

Figure 6:
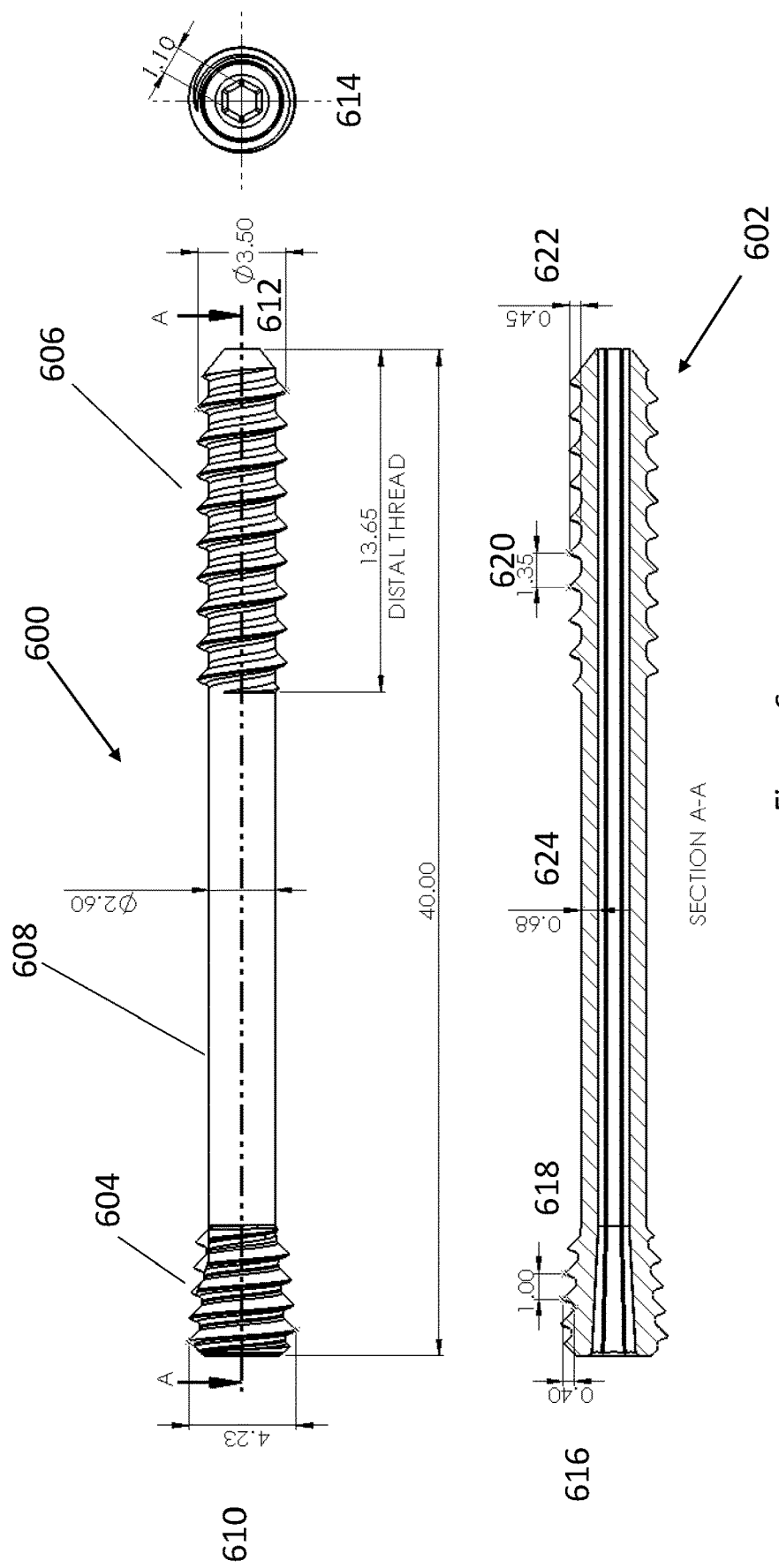
FIG. 6 shows a schematic drawing of an implant manufactured by with straight parallel fibers.

FIG. 6 shows a schematic drawing of an implant manufactured by with straight parallel fibers. As shown, an implant 600 is a two-dimensional schematic diagram (top) and is also shown as a cross-section 602, with the cross-section taken through A-A as shown (bottom). Turning now to implant 600, implant 600 features a plurality of proximal threads 604, a plurality of distal threads 606 and a shaft 608. A head 610 preferably has a width of 4.23 mm in this non-limiting example. A tip 612 preferably has a width of 3.50 mm in this non-limiting example. Distal thread 606 preferably has a length of 13.65 mm in this non-limiting example. A length of implant 600 is preferably 40.00 mm in this non-limiting example. A cross-sectional width of implant 600 is preferably 2.60 mm in this non-limiting example. A cross-section 614 shows a dimension of a hex driver along implant's cannula.

Turning now to cross-section 602, a height of the proximal threads 616 is preferably 0.40 mm while a distance between proximal threads 618 is preferably 1.0 mm in this non-limiting example. A height of the distal threads 622 is preferably 0.45 mm while a distance between distal threads 620 is preferably 1.35 mm in this non-limiting example. A cross-sectional width 624 is preferably 0.68 mm in this non-limiting example.

EXAMPLE 3: Helical & Straight Fibers Compression Screw Manufacturing Method

Manufacturing of a compression screw (CS) by with straight parallel fibers and helical fibers begin with material preparation. The process requires two different material preparation methods already explained in examples above: plates and strips. The ratio between parallel fiber plates weight and helical fibers strips in this example is 3.5:1 with a total weight of the implant of 0.465 grams, including compensation for material loss.

Plates of the raw material are cut to a length of an implant with original width and thickness. In this example the plates had the following dimensions: 6 plates of 40 mm length (fibers of full implant length), 13 mm width and 0.2 mm thickness; 2 plates of 15 mm length (chopped fibers), 13 mm width and 0.2 mm thickness; 4 plates of 5 mm length (chopped fibers), 13 mm width and 0.2 mm thickness. Quantity of pre-cut plates is such that their total weight is 0.360 grams.

Long thin strip of material was cut from a raw material spool. The strip in this example has the following dimensions: 2 mm width, 600 mm length and 0.2 mm thickness. The strip's total weight is 0.105 grams. Material composition as above.

Next stage of the manufacturing is material winding. The mandrel with a shape of CS cannula is fixed firmly in an electrical screw driver. Next, the pre-cut strip of the material is fixed to the mandrel using the same driver chuck at a constant angle of 20° relative to a plane perpendicular to CS axis. The strip is being heated with a stream of hot air from a blower at 300° C. exactly at the point where it meets the mandrel, in order to facilitate bending. In the same time, the mandrel starts to rotate in CCW direction (if viewed from a driver chuck) at a rate of 5-10 RPM. The angle between the material strip and the mandrel remains constant, as well as the pitch of the winding. When the material strip reaches the end of the mandrel, the winding begins in the opposite direction while the pitch and driver speed remain constant. When all the strips are wound on the mandrel, the mandrel is inserted into the mold.

Next, pre-cut plates are loaded into the mold all around the mandrel (full length plates and plates with chopped fibers are aligned in a fold as in FIG. 5) and the mold is inserted into the press. In this configuration there are five helical layers in the internal portion of the implant, two layers of 5 mm chopped fibers in a head region, one 15 mm chopped fibers layer in the distal thread region and six layers of full implant length fibers material along the implant length. The mold is heated to 120-130° C. and then the pressure of about 1150 bars is applied. The mold stays under pressure for 10 minutes while maintaining the heat in the same range. After that the mold is cooled to 30-37° C. and removed from a press. The implant is removed from a mold and continues to further processing. In this process the final implant has wound fibers in its core and straight parallel fibers in outer layers.

Table 3 shows implant performance test results:

| Test description | Testing method | Result value |
| --- | --- | --- |
| Bending strength | 3-point-bending as per ASTM D790 | 570 mPa |
| Pull-out force | per ASTM F2502 | 200N |
| Driving torque | per ASTM F2502 | 14N*cm |
| Maximal torque | per ASTM F2502 | 20N*cm |

Figure 7:
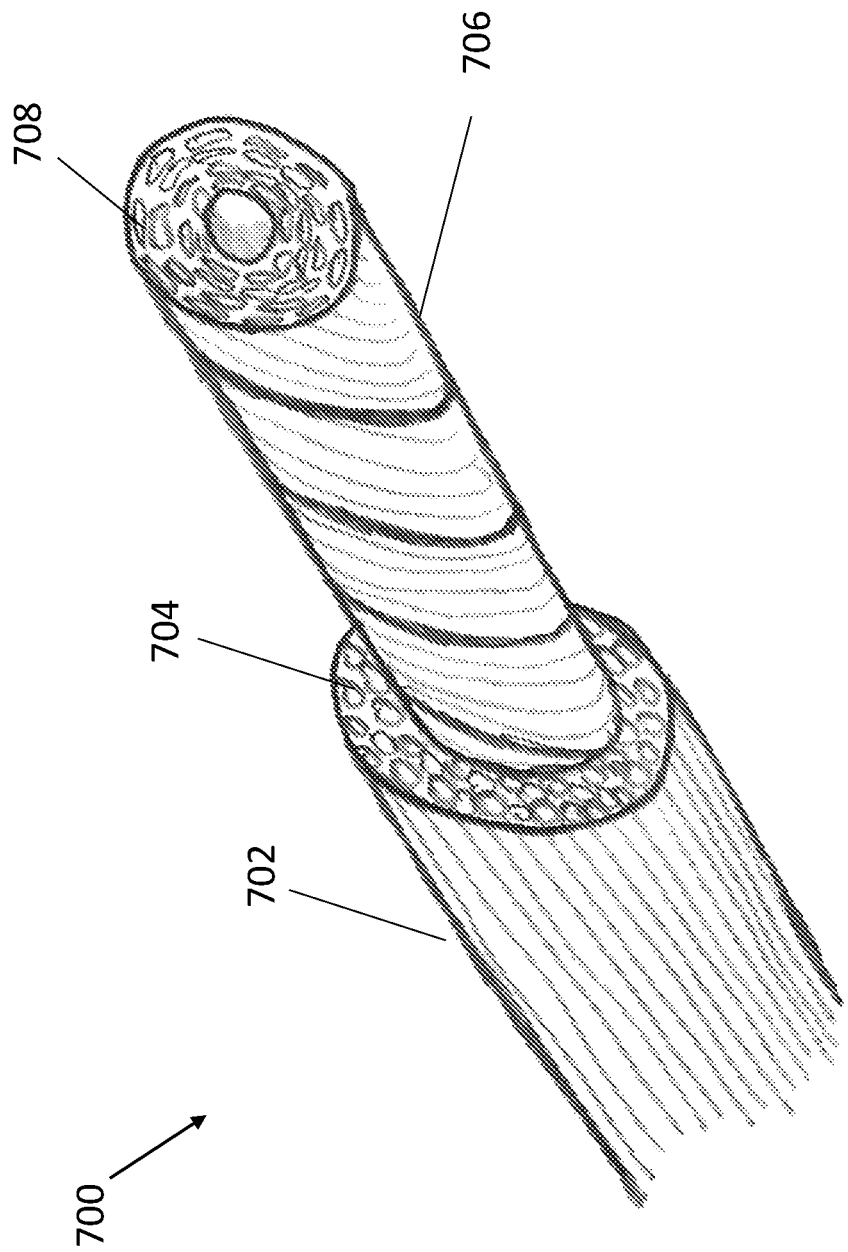
FIG. 7 is a schematic illustration of implant with fiber wound internal core and strait parallel fibers in outer shell.

FIG. 7 is a schematic illustration of implant with fiber wound internal core and straight parallel fibers in outer shell. An implant 700 features an outer shell 702 with a plurality of straight parallel fibers 704. Implant 700 also features an internal core 706, with a plurality of wound fibers 708.

Figure 8:
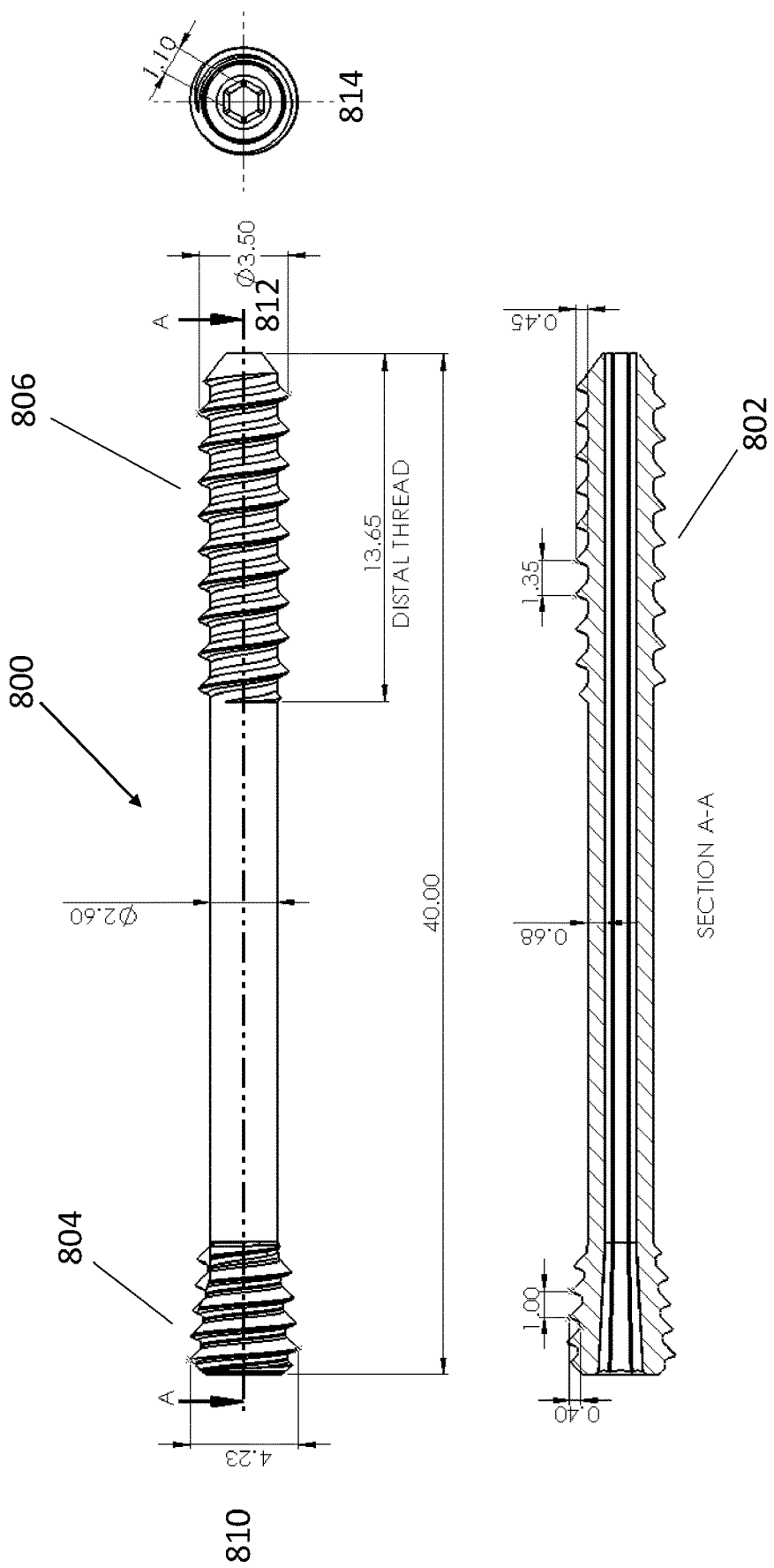
FIG. 8 shows a schematic drawing of an implant manufactured by with straight parallel fibers in outer shell and wound fibers in its core.

FIG. 8 shows a schematic drawing of an implant manufactured by with straight parallel fibers in outer shell and wound fibers in its core. As shown, an implant 800 is a two-dimensional schematic diagram (top) and is also shown as a cross-section 802, with the cross-section taken through A-A as shown (bottom). Turning now to implant 800, implant 800 features a plurality of proximal threads 804, a plurality of distal threads 806 and a shaft 808. A head 810 preferably has a width of 4.23 mm in this non-limiting example. A tip 812 preferably has a width of 3.50 mm in this non-limiting example. Distal thread 806 preferably has a length of 13.65 mm in this non-limiting example. A length of implant 800 is preferably 40.00 mm in this non-limiting example. A cross-sectional width of implant 800 is preferably 2.60 mm in this non-limiting example. A cross-section 814 shows a dimension of a hex driver along implant's cannula.

Turning now to cross-section 802, a height of the proximal threads 816 is preferably 0.40 mm while a distance between proximal threads 818 is preferably 1.0 mm in this non-limiting example. A height of the distal threads 822 is preferably 0.45 mm while a distance between distal threads 820 is preferably 1.35 mm in this non-limiting example. A cross-sectional width 824 is preferably 0.68 mm in this non-limiting example.

Figure 9:
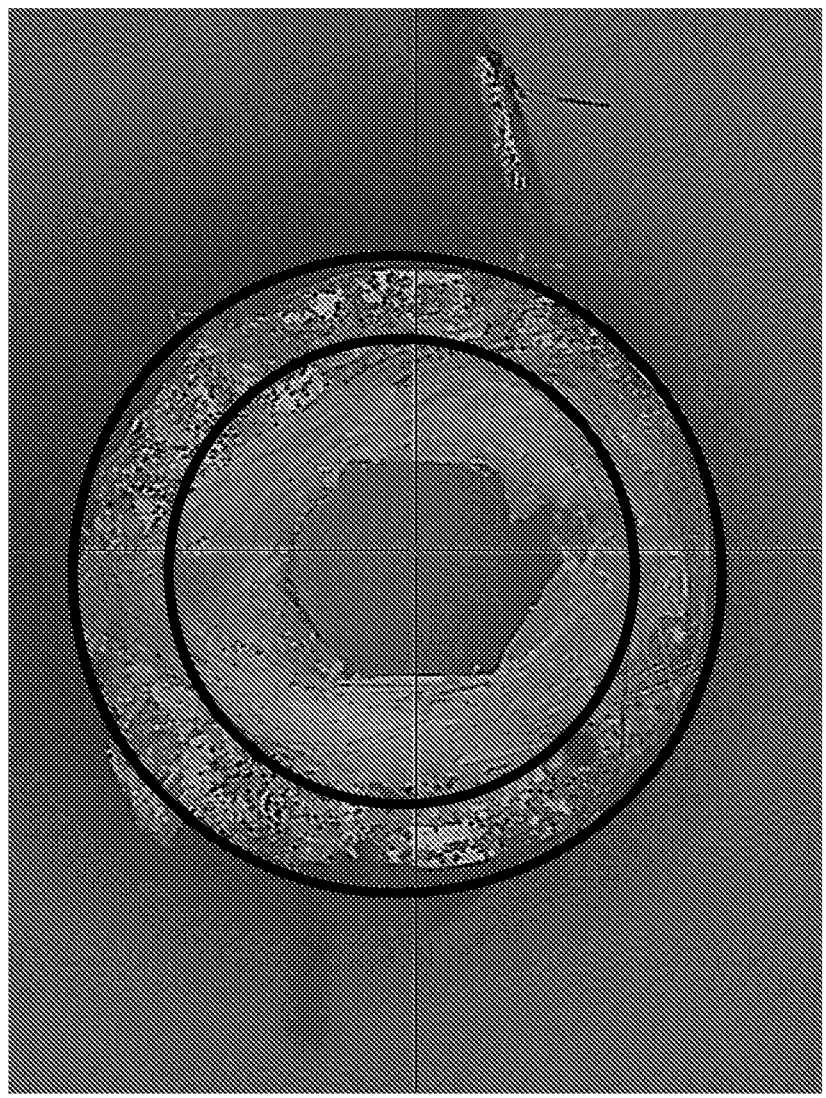
FIG. 9 shows a cross-section of an implant that shows straight parallel fibers in outer shell (area between red and blue circles) and wound fiber in a core (area inside a blue circle)

FIG. 9 shows a cross-section of an implant that shows straight parallel fibers in outer shell (area between red and blue circles) and wound fiber in a core (area inside a blue circle). Thickness of each concentric region is roughly ½ of implant's wall thickness.

Figure 10:
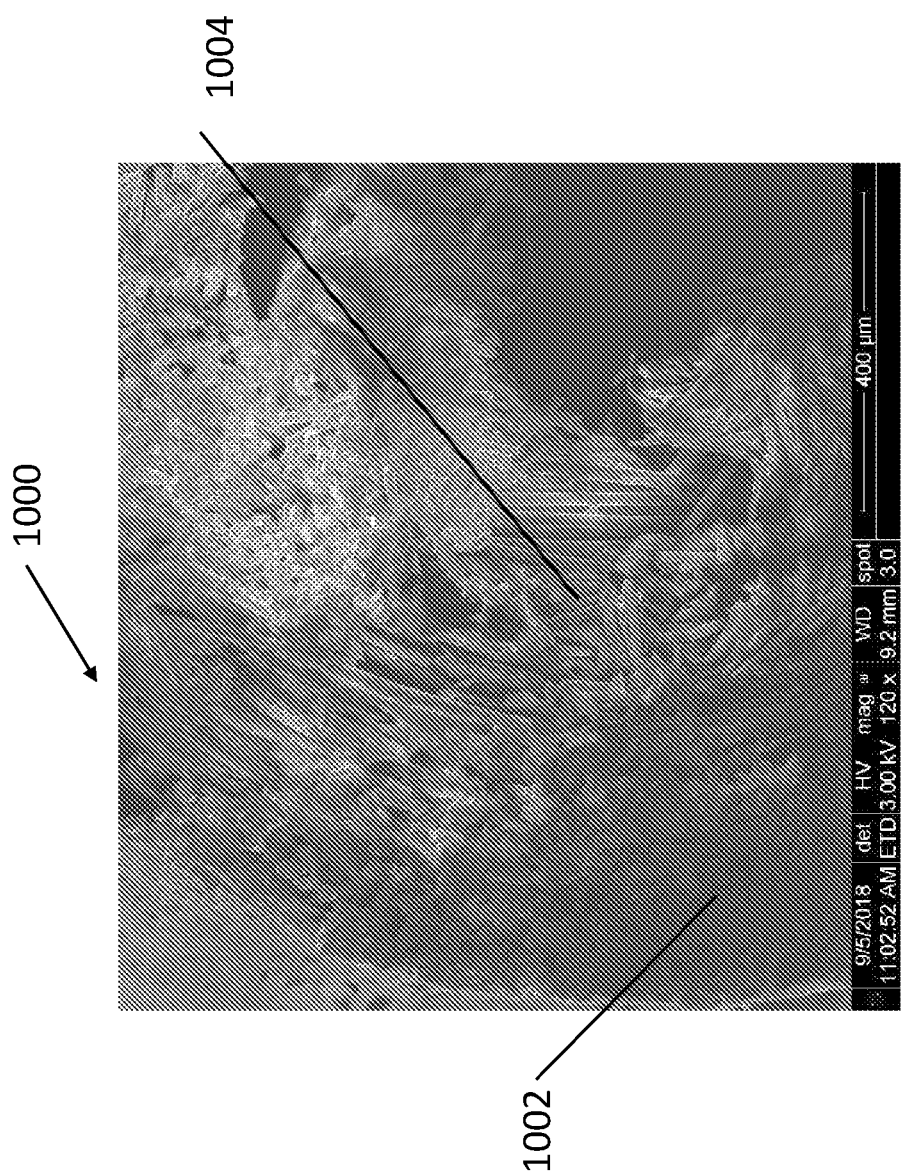
FIG. 10 shows an internal portion of an implant with helical layers and external portion with longitudinal layers.

FIG. 10 shows an internal portion of an implant with helical layers and external portion with longitudinal layers. As shown, an implant 1000 features external longitudinal layers 1002 and internal helical layers 1004.

Figure 11:
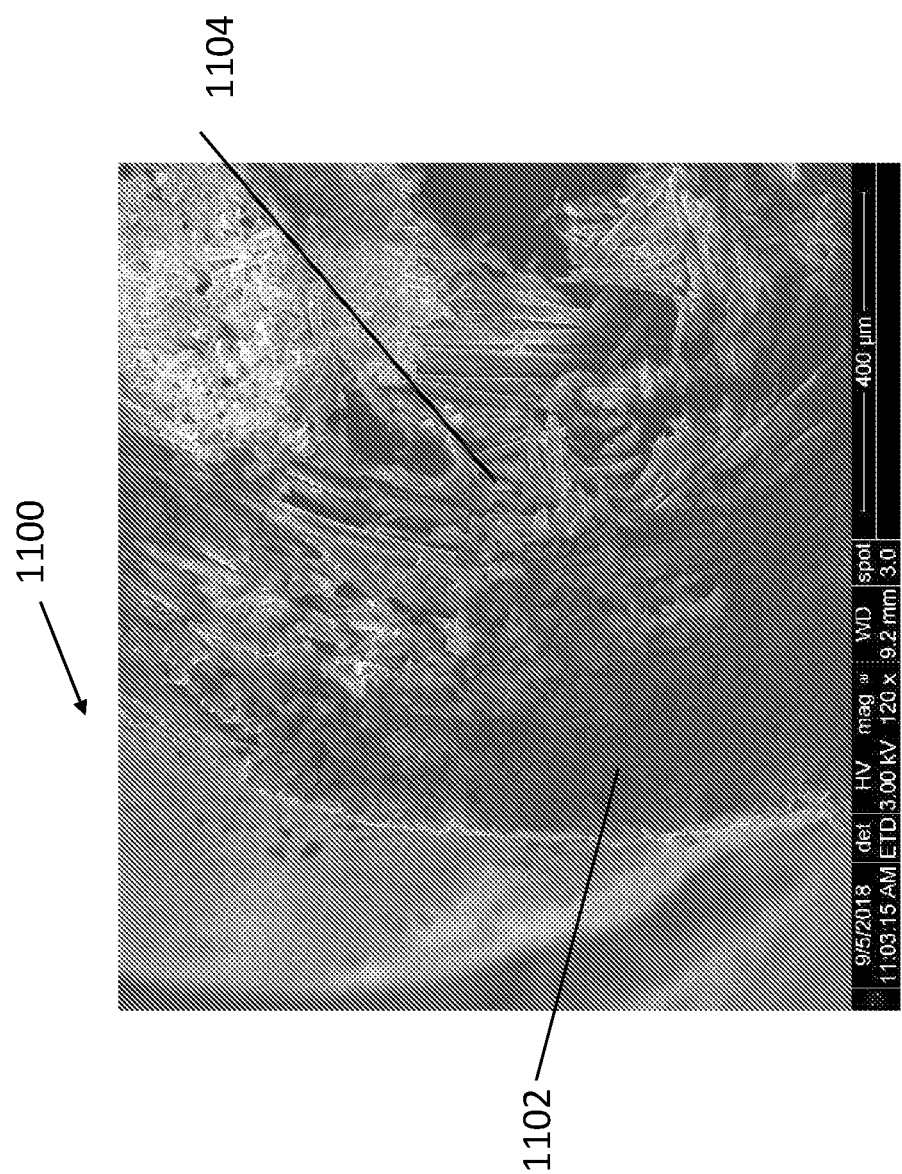
FIG. 11 shows an internal portion of an implant with helical layers and external portion with longitudinal layers.

FIG. 11 shows an internal portion of an implant with helical layers and external portion with longitudinal layers. As shown, an implant 1100 features external longitudinal layers 1102 and internal helical layers 1104.

It will be appreciated that various features of the invention which are, for clarity, described in the contexts of separate embodiments or as sub-embodiments may also be provided in combination in a single embodiment. Conversely, various features of the invention which are, for brevity, described in the context of a single embodiment may also be provided separately or in any suitable sub-combination. Any suitable combination of such features, embodiments and sub-embodiments may be made and is encompassed within the present invention. It will also be appreciated by persons skilled in the art that the present invention is not limited by what has been particularly shown and described hereinabove. Rather the scope of the invention is defined only by the claims which follow.

What is claimed is:

1. A medical implant comprising a biocomposite, said biocomposite comprising a polymer and a plurality of reinforcement fibers, wherein a weight percentage of a mineral composition within the biocomposite medical implant is in a range of 30-60%, wherein an average diameter of said fibers is in a range of 1-100 microns, said medical implant being threaded with a plurality of threads; wherein said fibers comprise a plurality of helical fibers and a plurality of longitudinal fibers; wherein a weight percentage to weight percentage ratio of said helical to said longitudinal fibers is from 90:10 to 10:90.

2. The implant of claim 1, wherein a winding angle of said helical layers is in a range of from 5 to 60 degrees or from 20 degrees to 45 degrees.

3. The implant of claim 1 wherein the implant threads are of a constant pitch or of a variable pitch.

4. The implant of claim 1, wherein said biocomposite is arranged in a plurality of layers, wherein fibers in each layer are discontinuous to an adjacent layer.

5. The implant of claim 4, wherein helical fibers in a first layer are wound clockwise while helical fibers in an adjacent layer are wound counterclockwise.

6. The implant of claim 5, wherein a winding angle of said helical fibers is wound toward an area of greater torsional stress of the implant.

7. The implant of claim 4, further comprising a plurality of helical layers and a plurality of longitudinal layers, wherein said helical and longitudinal layers are each grouped into discrete regions of wall thickness of the implant such that they form concentric regions in the implant.

8. The implant of claim 7, wherein a number of helical layers is in a range of from 1 to 15, preferably in the range of 1 to 10, more preferably in the range of 4 to 6, or optionally in the range of 8 to 15.

9. The implant of claim 8, wherein a diameter of the threaded implant is in the range of 2 to 4 mm and the number of helical layers is in the range of 2-12, preferably 3-8.

10. The implant of claim 8, wherein a number of longitudinal layers is in a range of from 1 to 15, preferably in the range of 1 to 10, more preferably in the range of 4-6, or optionally in the range of 1-5.

11. The implant of claim 1 further comprising at least one layer of a plurality of layers comprising a plurality of continuous fibers along said layer, and at least one other layer comprising a plurality of chopped fibers, wherein a length of said chopped fibers is less than a length of said at least one other layer.

12. The implant of claim 11, wherein an average length of the chopped fibers is <10% of the length of the implant and preferably <5% of the length of the implant.

13. The implant of claim 11, wherein of threads, and wherein said chopped fibers are located at said plurality of threads for reinforcement.

14. The implant of claim 1, wherein the plurality of threads form a single set of threads.

15. The implant of claim 1, comprising multiple sets of threads.

16. The implant of claim 1, comprising threads having a fixed lead or progressive lead.

17. The implant of claim 1, comprising threads having a fixed pitch or progressive pitch.

18. The implant of claim 1, wherein threading is not continuous throughout the circumference.

19. The implant of claim 1, wherein said plurality of threads comprise a shape selected from the group consisting of V thread, buttress, reverse buttress, spiral, combination of buttress and reverse, trapezoidal, square or a combination thereof.

20. The implant of claim 1 wherein an average depth of the threads is in the range of 0.2-4 mm.

21. The implant of claim 1 further comprising one or more longitudinal grooves breaking in the threads.

22. The implant of claim 21, wherein said one or more longitudinal grooves span an entire length of the plurality of threads.

23. The implant of claim 21, wherein said one or more longitudinal grooves span up to 80% of an entire length of the plurality of threads.

24. The implant of claim 1, wherein said mineral composition is silica-based.

25. The implant of claim 1, wherein density of the biocomposite composition is between 0.5 to 4 $g/cm^3$, between 1 to 3 $g/cm^3$, or between 1.3-2.5 $g/cm^3$.

26. The implant of claim 1, wherein mineral content is provided by a reinforcing mineral fiber made from the mineral composition.

27. The implant of claim 26, wherein said fibers are embedded in a polymer matrix comprising said biocomposite.

28. The implant of claim 27, wherein said polymer comprises lactide, glycolide, caprolactone, valerolactone, carbonates (e.g., trimethylene carbonate, tetramethylene carbonate, and the like), dioxanones (e.g., 1,4-dioxanone), δ-valerolactone, 1, dioxepanones e.g., 1,4-dioxepan-2-one and 1,5-dioxepan-2-one), ethylene glycol, ethylene oxide, esteramides, γ-ydroxyvalerate, β-hydroxypropionate, alpha-hydroxy acid, hydroxybuterates, poly (ortho esters), hydroxy alkanoates, tyrosine carbonates, polyimide carbonates, polyimino carbonates such as poly (bisphenol A-iminocarbonate) and poly (hydroquinone-iminocarbonate, (polyurethanes, polyanhydrides, polymer drugs (e.g., polydiflunisol, polyaspirin, and protein therapeutics), sugars; starch, cellulose and cellulose derivatives, polysaccharides, collagen, chitosan, fibrin, hyaluronic acid, polypeptides, proteins, poly (amino acids), polylactides (PLA), poly-L-lactide (PLLA), poly-DL-lactide (PDLLA); polyglycolide (PGA); copolymers of glycolide, glycolide/trimethylene carbonate copolymers (PGA/TMC); other copolymers of PLA, such as lactide/tetramethylglycolide copolymers, lactide/trimethylene carbonate copolymers, lactide/d-valerolactone copolymers, lactide/c-caprolactone copolymers, L-lactide/DL-lactide copolymers, glycolide/L-lactide copolymers (PGA/PLLA), polylactide-co-glycolide; terpolymers of PLA, such as lactide/glycolide/trimethylene carbonate terpolymers, lactide/glycolide/ε-caprolactone terpolymers, PLA/polyethylene oxide copolymers; polydepsipeptides; unsymmetrically 3,6-substituted poly-1,4-dioxane-2,5-diones; polyhydroxyalkanoates; such as polyhydroxybutyrates (PHB); PHB/b-hydroxyvalerate copolymers (PHB/PHV); poly-b-hydroxypropionate (PHPA); poly-p-dioxanone (PDS); poly-d-valerolactone -poly-ε-capralactone, poly(ε-caprolactone-DL-lactide) copolymers; methylmethacrylate-N-vinyl pyrrolidone copolymers; polyesteramides; polyesters of oxalic acid; polydihydropyrans; polyalkyl-2-cyanoacrylates; polyurethanes (PU); polyvinylalcohol (PVA); polypeptides; poly-b-malic acid (PMLA): poly-b-alkanbic acids; polycarbonates; polyorthoesters; polyphosphates; poly(ester anhydrides); and mixtures thereof; and derivatives, copolymers and mixtures thereof.

29. A method of treatment for an orthopedic application in a subject in need of treatment thereof, comprising implanting to the subject the medical implant of claim 1.

30. The method of treatment of claim 29, wherein said implanting to the subject comprises performing structural fixation for a load-bearing purpose within the subject.

31. The method of treatment of claim 29, where said performing structural fixation comprises performing bone fixation.

* * * * *